(12) United States Patent  
Mellier

(10) Patent No.: US 8,753,260 B2
(45) Date of Patent: *Jun. 17, 2014

(54) PROLAPSE REPAIR

(75) Inventor: Georges Mellier, Lyons (FR)

(73) Assignee: AMS Research Corporation, Minnetonka, MN (US)

( * ) Notice: Subject to any disclaimer, the term of this patent is extended or adjusted under 35 U.S.C. 154(b) by 309 days.

This patent is subject to a terminal disclaimer.

(21) Appl. No.: 13/235,694

(22) Filed: Sep. 19, 2011

(65) Prior Publication Data

US 2012/0010457 A1 Jan. 12, 2012

Related U.S. Application Data

(63) Continuation of application No. 12/021,092, filed on Jan. 28, 2008, now Pat. No. 8,038,594, which is a continuation of application No. 10/804,718, filed on Mar. 19, 2004, now Pat. No. 7,347,812.

(60) Provisional application No. 60/545,987, filed on Feb. 19, 2004, provisional application No. 60/504,755, filed on Sep. 22, 2003.

(51) Int. Cl.
*A61F 2/02* (2006.01)

(52) U.S. Cl.
USPC .......................................................... 600/30

(58) Field of Classification Search
USPC ................................ 600/29–32; 128/897, 898
See application file for complete search history.

(56) References Cited

U.S. PATENT DOCUMENTS

| | | | |
|---|---|---|---|
| 2,738,790 A | 3/1956 | Todt et al. |
| 3,124,136 A | 3/1964 | Usher |
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,204,541 A | 5/1980 | Kapitanov |

(Continued)

FOREIGN PATENT DOCUMENTS

DE 23 05 815 A1 8/1974
DE 42 20 283 C2 12/1993

(Continued)

OTHER PUBLICATIONS

"Urinary Incontinence: Easier Operation" Article from La Libre Belgique, Wednesday, Oct. 25, 2003 (English translation provided).

(Continued)

*Primary Examiner* — Samuel Gilbert
(74) *Attorney, Agent, or Firm* — Gregory L. Koeller

(57) ABSTRACT

Surgical instruments for prolapse repair are disclosed. The surgical instruments have straight portions and helical portions.

17 Claims, 19 Drawing Sheets

(56) References Cited

U.S. PATENT DOCUMENTS

| | | | |
|---|---|---|---|
| 4,235,238 A | 11/1980 | Ogiu et al. |
| 4,246,660 A | 1/1981 | Wevers |
| 4,265,231 A | 5/1981 | Scheller, Jr. et al. |
| 4,441,497 A | 4/1984 | Paudler |
| 4,509,516 A | 4/1985 | Richmond |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,920,986 A | 5/1990 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,188,636 A | 2/1993 | Fedotov |
| 5,207,694 A | 5/1993 | Broome |
| 5,209,756 A | 5/1993 | Seedhom et al. |
| 5,250,033 A | 10/1993 | Evans et al. |
| 5,256,133 A | 10/1993 | Spitz |
| 5,281,237 A | 1/1994 | Gimpelson |
| 5,328,077 A | 7/1994 | Lou |
| 5,336,239 A | 8/1994 | Gimpelson |
| 5,337,736 A | 8/1994 | Reddy |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,520,700 A | 5/1996 | Beyar et al. |
| 5,520,703 A | 5/1996 | Essig et al. |
| 5,544,664 A | 8/1996 | Benderev et al. |
| 5,562,685 A | 10/1996 | Mollenauer et al. |
| 5,562,689 A | 10/1996 | Green et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,633,286 A | 5/1997 | Chen |
| 5,662,683 A | 9/1997 | Kay |
| 5,669,935 A | 9/1997 | Rosenman et al. |
| 5,683,349 A | 11/1997 | Makower et al. |
| 5,807,403 A | 9/1998 | Beyar et al. |
| 5,810,882 A | 9/1998 | Bolduc et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,904,696 A | 5/1999 | Rosenman |
| 5,919,232 A | 7/1999 | Chaffringeon et al. |
| 5,934,283 A | 8/1999 | Willem et al. |
| 5,935,122 A | 8/1999 | Fourkas et al. |
| 5,935,138 A | 8/1999 | McJames, II et al. |
| 5,944,732 A | 8/1999 | Raulerson et al. |
| 5,972,000 A | 10/1999 | Beyar et al. |
| 5,988,171 A | 11/1999 | Sohn et al. |
| 5,992,269 A | 11/1999 | Puig et al. |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,042,534 A | 3/2000 | Gellman et al. |
| 6,042,536 A | 3/2000 | Tihon et al. |
| 6,048,351 A | 4/2000 | Gordon et al. |
| 6,050,937 A | 4/2000 | Benderev |
| 6,053,935 A | 4/2000 | Brenneman et al. |
| 6,068,591 A | 5/2000 | Bruckner et al. |
| 6,071,290 A | 6/2000 | Compton |
| 6,099,538 A | 8/2000 | Moses et al. |
| 6,106,545 A | 8/2000 | Egan |
| 6,110,101 A | 8/2000 | Tihon et al. |
| 6,117,067 A | 9/2000 | Gil-Vernet |
| 6,168,611 B1 | 1/2001 | Risvi |
| 6,221,005 B1 | 4/2001 | Bruckner et al. |
| 6,273,852 B1 | 8/2001 | Lehe et al. |
| 6,302,840 B1 | 10/2001 | Benderev |
| 6,306,079 B1 | 10/2001 | Trabucco |
| 6,328,744 B1 | 12/2001 | Harari et al. |
| 6,334,446 B1 | 1/2002 | Beyar |
| 6,352,553 B1 | 3/2002 | van de Burg et al. |
| 6,367,353 B2 | 4/2002 | Brucart Puig et al. |
| 6,382,214 B1 | 5/2002 | Raz et al. |
| 6,406,423 B1 | 6/2002 | Scetbon |
| 6,406,480 B1 | 6/2002 | Beyar et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,494,906 B1 | 12/2002 | Owens |
| 6,502,578 B2 | 1/2003 | Raz et al. |
| 6,530,943 B1 | 3/2003 | Hoepffner et al. |
| 6,582,443 B2 | 6/2003 | Cabak et al. |
| 6,626,917 B1 | 9/2003 | Craig |
| 6,663,633 B1 | 12/2003 | Pierson, II |
| 6,911,003 B2 * | 6/2005 | Anderson et al. ............ 600/30 |
| 7,204,802 B2 | 4/2007 | De Leval |
| 7,347,812 B2 * | 3/2008 | Mellier ........................ 600/29 |
| 2001/0000533 A1 | 4/2001 | Kovac |
| 2001/0049467 A1 | 12/2001 | Lehe et al. |
| 2002/0022841 A1 | 2/2002 | Kovac |
| 2002/0028980 A1 | 3/2002 | Thierfelder et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0099260 A1 | 7/2002 | Suslaine et al. |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0165566 A1 | 11/2002 | Ulmsten |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023137 A1 | 1/2003 | Gellman |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0045892 A1 | 3/2003 | Kaladelfos |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0100954 A1 | 5/2003 | Schuldt-Hempe et al. |
| 2003/0114866 A1 | 6/2003 | Ulmsten et al. |
| 2003/0130670 A1 | 7/2003 | Anderson et al. |
| 2003/0149440 A1 | 8/2003 | Kammerer et al. |
| 2003/0171644 A1 | 9/2003 | Anderson et al. |
| 2003/0176762 A1 | 9/2003 | Kammerer |
| 2003/0199732 A1 | 10/2003 | Suslian et al. |
| 2003/0220538 A1 | 11/2003 | Jacquetin |
| 2004/0039453 A1 | 2/2004 | Anderson et al. |

FOREIGN PATENT DOCUMENTS

| | | |
|---|---|---|
| DE | 43 04 353 A1 | 4/1994 |
| DE | 101 38 950 A1 | 2/2003 |
| DE | 102 11 360 A1 | 10/2003 |
| EP | 0 470 308 A1 | 2/1992 |
| EP | 0 643 945 A2 | 3/1995 |

(56) References Cited

FOREIGN PATENT DOCUMENTS

| | | |
|---|---|---|
| EP | 0 650 703 A1 | 5/1995 |
| EP | 1 093 758 A1 | 4/2001 |
| SU | 1225547 A | 4/1986 |
| SU | 1342486 A1 | 10/1987 |
| WO | WO 93/17635 A1 | 3/2000 |
| WO | WO 93/19678 A2 | 4/2000 |
| WO | WO 97/16121 A1 | 10/2000 |
| WO | WO 00/64370 A1 | 11/2000 |
| WO | WO 98/35632 A | 11/2000 |
| WO | WO 00/74594 A1 | 12/2000 |
| WO | WO 00/74613 A1 | 12/2000 |
| WO | WO 00/74633 A2 | 12/2000 |
| WO | WO 98/19606 A1 | 12/2000 |
| WO | WO 98/35606 A2 | 12/2000 |
| WO | WO 98/35616 A1 | 12/2000 |
| WO | WO 01/26581 A1 | 4/2001 |
| WO | WO 98/35632 A1 | 4/2001 |
| WO | WO 00/13601 A1 | 6/2001 |
| WO | WO 01/39670 A1 | 6/2001 |
| WO | WO 01/45589 A1 | 6/2001 |
| WO | WO 01/56499 A1 | 6/2001 |
| WO | WO 99/52450 A1 | 6/2001 |
| WO | WO 00/18319 A1 | 8/2001 |
| WO | WO 00/57812 A1 | 10/2001 |
| WO | WO 01/78609 A2 | 10/2001 |
| WO | WO 02/26108 A2 | 4/2002 |
| WO | WO 02/28312 A1 | 4/2002 |
| WO | WO 02/32284 A2 | 4/2002 |
| WO | WO 02/34124 A2 | 5/2002 |
| WO | WO 02/38079 A2 | 5/2002 |
| WO | WO 02/39890 A2 | 5/2002 |
| WO | WO 02/019944 A2 | 9/2002 |
| WO | WO 02/069781 A2 | 9/2002 |
| WO | WO 02/071953 A2 | 9/2002 |
| WO | WO 02/002031 A1 | 10/2002 |
| WO | WO 02/078552 A1 | 10/2002 |
| WO | WO 2004/016196 A2 | 2/2004 |
| WO | WO 2004/019786 A1 | 3/2004 |

OTHER PUBLICATIONS

Aldridge, Albert H., B.S., M.D., F.A.C.S., "Transplantation of Fascia for Relief of Urinary Stress Incontinence" Am. J. of Obstet. and Gynec., vol. 44, pp. 398-411 (1948).
Araki, Tohru, et al, "The Loop-Loosening Procedure for Urination Difficulties After Stamey Suspension of the Vesical Neck" The Journal of Urology, vol. 144, pp. 319-323, (Aug. 1990) American Urological Association, Inc.
Asmussen, M., et al., "Simultaneous Urethro-Cystometry With a New Technique" Scand J Urol Nephrol 10, pp. 7-11 (1976).
Beck, Peter R. et al., "Treatment of Urinary Stress Incontinence With Anterior Colporrhaphy" Obstetrics and Gynecology, vol. 59 (No. 3), pp. 269-274 (Mar. 1982).
Benderev, Theodore V., M.D., "Anchor Fixation and Other Modifications of Endoscopic Bladder Neck Suspension" Urology, vol. 40, No. 5, pp, 409-418 (Nov. 1992).
Benderev, Theodore V., MD, "A Modified Percutaneous Outpatient Bladder Neck Suspension System" Journal of Urology, vol. 152, pp. 2316-2320 (Dec. 1994).
Bergman, Arieh, M.D. et al., "Three surgical procedures for genuine stress incontinence: Five-year follow-up of a prospective randomized study" Am. J. Obstet Gynecol, vol. 173 No. 1, pp. 66-71 (Jul. 1995).
Blaivas, Jerry G., "Commentary: Pubovaginal Sling Procedure" Surgery for Female Urinary Incontinence, pp. 93-101 (1990).
Blaivas, Jerry G. et al., "Pubovaginal Fascial Sling for the Treatment of Complicated Stress Urinary Incontinence" The Journal of Urology, vol. 145, pp. 1214-1218 (Jun. 1991) American Urological Association, Inc.
Blaivas, Jerry G., M.D., et al., "Type III Stress Urinary Incontinence: Importance of Proper Diagnosis and Treatment" Gynecology and Obstetrics Surgical Forum , 35, pp. 473-475 (1984).

Bryans, Fred E., M.D., F.R.C.S.(C.), "Marlex gauze hammock sling operation with Cooper's ligament attachment in the management of recurrent urinary stress incontinence" Am. J. Obstet. Gynecol., vol. 133, No. 3, pp. 292-294 (Feb. 1, 1979).
Burch, John C., M.D., "Urethrovaginal fixation to Cooper's ligament for correction of stress incontinence, cystocele, and prolapse" Am. J. Obstet. & Gynecol., vol. 81 No. 2, pp. 281-290 (Feb. 1961).
Choe, Jong M., et al., "Gore-Tex Patch Sling: 7 Years Later" Urology, 54 (4) pp. 641-646 (1999) Elsevier Science Inc.
Chu, C.C., and Welch, L., "Characterization of Morphologic and Mechanical Properties of Surgical Mesh Fabrics" Journal of Biomedical Materials Research, vol. 19, pp. 903-916 (1985) © 1985 John Wiley & Sons, Inc.
Dargent, D., et al. Pose d'un ruban sous uretral oblique par vole obturatrice dans le traitement de l'incontinence urinaire feminine, Gynecol Obstet Fertil 2002; 30: pp. 576-582 (2002) (English translation provided).
Das, Sakti et al., "Laparoscopic Colpo-Suspension" The Journal of Urology, vol. 154, pp. 1119-1121 (Sep. 1995).
de Leval, Jean "Novel Surgical Technique for the Treatment of Female Stress Urinary Incontinence: Transobturator Vaginal Tape Inside-Out" European Urology 44 pp. 724-730 (2003).
Decter, Ross M., "Use of the Fascial Sling for Neurogenic Incontinence: Lessons Learned" The Journal of Urology, vol. 150, pp. 683-686, (Aug. 1993) American Urological Association, Inc.
DeLancey, John O. L., M.D., "Structural support of the urethra as it relates to stress urinary incontinence: The hammock hypothesis" Am. J Obstet Gynecol, pp. 1713-1723 (Jun. 1994).
Delorme, "La bandelette trans-obturatrice: un procede mini-invasif pour traiter l'incontinence urinaire d'effort de la femme", Urologie de la Femme, Proges en Urologie (2001), 11, 1306-1313 (Sep. 2001) (English translation provided).
Delorme, Emmanuel et al., "Transobturator Tape (Uratape®): A New Minimally-Invasive Procedure to Treat Female Urinary Incontinence" European Urology 45 (2004) 203-207 (Dec. 2003).
Dietz, H.P., et al., "Mechanical Properties of urogynecologic Implant Materials" International Urogynecology Journal (2003) 14:239-243 (Aug. 5, 2003).
Enzelsberger, H., et al., "Urodynamic and Radiologic Parameters Before and After Loop Surgery for Recurrent Urinary Stress Incontinence" Acta Obstet Gynecol Scand 1990; 69 pp. 51-54 (1990).
Eriksen, Bjarne C. et al., "Long-Term Effectiveness of the Burch Colposuspension in Female Urinary Stress Incontinence" Acta Obstet Gynecol Scand 1990; 69 pp. 45-50 (1990).
Falconer, C. et al., "Clinical Outcome and Changes in Connective Tissue Metabolism After Intravaginal Slingplasty in Stress Incontinent Women" International Urogynecol J, vol. 7, pp. 133-137, (1996).
Falconer, C., et al., "Influence of Different Sling Materials on Connective Tissue Metabolism in Stress Urinary Incontinent Women" International Urogynecology Journal, (2001) (Supp. 2) pp. S19-S21 (2001).
Gilja, Ivan et all, "A Modified Raz Bladder Neck Suspension Operation (Transvaginal Burch)" The Journal of Urology, vol. 153, pp. 1455-1457 (May 1995).
Gittes, Ruben F., et al, "No-Incision Pubovaginal Suspension for Stress Incontinence" The Journal of Urology, vol. 138, pp. 568-570 (Sep. 1987).
Handa, Victoria L., M.D. et al., "Banked Human Fascia Lata for the Suburethral Sling Procedure: A Preliminary Report" Obstetrics and Gynecology, vol. 88, No. 6, pp. 1045-1049 (Dec. 1996).
Henriksson, L., M.D. et al., "A urodynamic evaluation of the effects of abdominal urethrocystopexy and vaginal sling urethroplasty in women with stress incontinence" Am. J. Obstet. Gynecol, pp. 77-82 (May 1, 1978).
Hershorn, Sender, M.D. et al., "Gynecare TVT With Abdominal Guides Early Clinical Experience" Gynecare TVT, Marketing Material, Gynecare Windows (May 2002), 12 pages.
Hodgkinson, C. Paul, M.D., et al., "Urinary Stress Incontinence in the Female—III. Round-ligament technic for retropubic suspension of the urethra" Obstetrics and Gynecology, vol. 10, No. 5, pp. 493-499 (Nov. 1957).

(56) References Cited

OTHER PUBLICATIONS

Hohenfellner, Rudolf, et al., "Sling Procedures" Surgery of Female Incontinence-Second Edition, Chapter 7, pp. 105-113, Springer-Verlag (May 1, 1986).

Holschneider, C.H., et al., "The Modified Pereyra Procedure in Recurrent Stress Urinary Incontinence: A 15-year Review" Obstetrics & Gynecology, vol. 83, No. 4, pp. 573-578 (Apr. 1994).

Horbach, Nicollette S., "Suburethral Sling Procedures" Urolgynecology and Urodynamics Theory and Practice, Fourth Edition, Chapter 42, pp. 569-579, Williams & Wilkins (1996).

Horbach, Nicollette S., et al., "A Suburethral Sling Procedure with Polytetrafluoroethylene for the Treatment of Genuine Stress Incontinence in Patients with Low Urethral Closure Pressure" Obstetrics & Gynecology, vol. 71, No. 4, pp. 648-652 (Apr. 1988).

Iglesia, C.B., et al., "The Use of Mesh in Gynecologic Surgery" International Urogynecology Journal (1997) 8:105-115, Springer-Verlag London Ltd. (1997).

Ingelman-Sundberg, A., et al., "Surgical Treatment of Female Urinary Stress Incontinence" Contr. Gynec. Obstet. vol. 10, pp. 51-69 (Karger. Basel 1983).

Jeffcoate, T. N. A., M.D., F.R.C.S.E., F.R.C.O.G., "The Results of the Aldridge Sling Operation for Stress Incontinence" J Obstet Gynaecol Br Emp., 63(1) pp. 36-39 (Feb. 1956).

Karram, Mickey M., M.D. et al., "Patch Procedure: Modified Transvaginal Fascia Lata Sling for Recurrent or Severe Stress Urinary Incontinence" Obstetrics & Gynecology, vol. 75, No. 3, Part 1, pp. 461-463 (Mar. 1990).

Kersey, J., "The gauze hammock sling operation in the treatment of stress incontinence" British Journal of Obstetrics and Gynaecology, vol. 90 pp. 945-949, (Oct. 1983).

Klutke, Carl et al., "The Anatomy of Stress Incontinence: Magentic Resonance Imaging of the Female Bladder Neck and Urethra" The Journal Urology, vol. 143, pp. 563-566 (Mar. 1990).

Klutke, John James et al., "Transvaginal Bladder Neck Suspension to Cooper's Ligament: A Modified Pereyra Procedure" Obstetrics & Gynecology, vol. 88, No. 2, pp. 294-296 (Aug. 1996).

Klutke, John, M.D. et al., "The promise of tension-free vaginal tape for female SUI" Contemporary Urology, pp. 59-60, 65-66, 69-70, 73 (Oct. 2000).

Korda, Andrew, et al., "Experience with Silastic Slings for Female Urinary Incontinence" Aust NZ J Obstet Gynaecol, vol. 29, pp. 150-154 (1989).

Kovac, S. Robert, et al, "Pubic Bone Suburethral Stabilization Sling for Recurrent Urinary Incontinence" Obstetrics & Gynecology, vol. 89, No. 4, pp. 624-627 (Apr. 1997).

Kovac, S. Robert, et al, "Pubic Bone Suburethral Stabilization Sling: A Long Term Cure for SUI?" Contemporary OB/GYN, 8 pages (Feb. 1998).

Kovac, S. Robert, "Follow-up of the Pubic Bone Suburethral Stabilization Sling Operation for Recurrent Urinary Incontinence (Kovac Procedure)" Journal of Pelvic Surgery, pp. 156-160 (May 1999).

Leach, Gary E., et al, "Female Stress Urinary Incontinence Clinical Guidelines Panel Report on Surgical Management of Female Stress Urinary Incontinence" American Urological Association, vol. 158, pp. 875-880 (Sep. 1997).

Leach, Gary E., MD, "Bone Fixation Technique for Transvaginal Needle Suspension" Urology vol. XXXI, No. 5, pp. 383-390 (May 1988).

Letters to the Editor, R. Villet's response to the article by D. Dargent et al., "Placement of an oblique transobturator suburethral tape in the treatment of female urinary incontinence", Gynecology Obstetrics & Fertility 31, pp. 96-101 (2003) (English translation provided).

Lichtenstein, Irving L., M.D., et al., "The Tension-Free Hernioplasty" The American Journal of Surgery, vol. 157, pp. 188-193 (Feb. 1989).

Loughlin, Kevin R., et al., "Review of an 8-Year Experience With Modifications of Endoscopic Suspension of the Bladder Neck for Female Stress Urinary Incontinence" The Journal of Urology, vol. 143, pp. 44-45 (Jan. 1990).

Marshall, Victor Fray, M.D., F.A.C.S. et al., "The Correction of Stress Incontinence by Simple Vesicourethral Suspension" Surgery, Gynecology and Obstetrics, vol. 88, pp. 509-518 (1949).

Mascio, Valenzio C., M.D., "Therapy of Urinary Stress Incontinence in Women Using Mitek GII Anchors" Mitek Surgical Products, Inc., 5 pages (1993).

McGuire, Edward J. et al., "Abdominal Fascial Slings" Female Urology 2nd ed. (Raz. S. ed.). W.B. Saunders Company, Chapter 31, pp. 369-375 (1996).

McGuire, Edward J. et al., "Experience With Pubovaginal Slings for Urinary Incontinence at the University of Michigan" The Journal of Urology, vol. 138, pp. 525-526 (Sep. 1987).

McGuire, Edward J., et al., "Pubovaginal Sling Procedure for Stress Incontinence" The Journal of Urology, vol. 119, pp. 82-84 (Jan. 1978) The Williams & Wilkins Co.

McGuire, Edward J., M.D., "Abdominal Procedures for Stress Incontinence" Symposium on Female Urology, Urologic Clinics of North America—vol. 12, No. 2, pp. 285-290 (May 1985).

McIndoe, G. A. J., et al., "The Aldridge Sling Procedure in the Treatment of Urinary Stess Incontinence" Aust NZ J Obstet Gynaecol, vol. 27, pp. 238-239 (1987).

McKiel, Charles F., Jr. et al., "Marshall-Marchetti Procedure: Modification" 1st Journal in Urology, vol. 96, pp. 737-739 (Nov. 1966) The Williams & Wilkins Co.

Moir, J. Chassar, "The Gauze-Hammock Operation (A Modified Aldridge Sling Prcedure)" The Journal of Obstetrics and Gynaecology of the British Commonwealth, vol. 75 No. 1, pp. 1-9 (Jan. 1968).

Morgan, J.E., M.D. et al., "The Marlex Sling Operation for the Treatment of Recurrent Stress Urinary Incontinence: A 16-Year Review", Am. J. Obstet. Gynecol., vol. 151, No. 2, pp. 224-226 (Jan. 15, 1985).

Morgan, J.E., M.D., "A sling operation, using Marlex Polypropylene mesh, for treatment of recurrent stress incontinence", Amer. J. Obstet. Gynecol., vol. 106, No. 3, pp. 369-377 (Feb. 15, 1970).

Narik, G., M.D., "A simplified sling operation suitable for routine use" Am. J. Obst. & Gynec., vol. 84, No. 3, pp. 400-405 (Aug. 1, 1962).

Nichols, David H., Md, Facog, "The Mersilene Mesh Gauze-Hammock for Severe Urinary Stress Incontinence" Obstetrics and Gynecology, vol. 41, No. 1, pp. 88-93 (Jan. 1973)

Nickel, Rafael F., et al., "Evaluation of a Transpelvic Sling Procedure With and Without Colposuspension for Treatment of Female Dogs With Refractory Urethral Sphincter Mechanism Incompetence" Veterinary Surgery, vol. 27, pp. 94-104, (1998), The American College of Veterinary Surgeons.

Norris, Jeffrey P., M.D., et al., "Use of Synthetic Material in Sling Surgery: A Minimally Invasive Approach" Journal of Endourology, vol. 10 No. 3, pp. 227-230 (Jun. 1996) Mary Ann Liebert, Inc.

O'Donnell, Pat D., M.D., "Combined Raz Urethral Suspension and McGuire Pubovaginal Sling For Treatment of Complicated Stress Urinary Incontinence" Journal of The Arkansas Medical Society, vol. 88, No. 8, pp. 389-392 (Jan. 1992).

Parra, R. O., et al., "Experience with a Simplified Technique for the Treatment of Female Stress Urinary Incontinence" British Journal of Urology, vol. 66, pp. 615-617 (1990).

Pelosi, Marco A., II, et al., "New Tranobturator Sling Reduces Risk of Injury" OBG Management, pp. 17-20, 30, 32, 35-38 (Jul. 2003).

Pelosi, Marco Antonio III et al., "Pubic Bone Suburethral Stabilization Sling: Laparoscopic Assessment of a Transvaginal Operation for the Treatment of Stress Urinary Incontinence" Journal of Laparoendoscopic & Advanced Surgical Techniques, vol. 9, No. 1 pp. 45-50 (1999).

Pereyra, Armand J. et al, "Pubourethral Supports in Perspective: Modified Pereyra Procedure for Urinary Incontinence" Obstetrics and Gynecology, vol. 59, No. 5, pp. 643-648 (May 1982).

Pereyra, Armand J., M.D., F.A.C.S., "A Simplified Surgical Procedure for the Correction of Stress Incontinence in Women" West J. Surg. Obst. & Gynec. pp. 223-226 (Jul.-Aug. 1959).

Petros, P. E. Papa, "Medium-term Follow-up of the Intravaginal Slingplasty Operation Indicates Minimal Deterioration of Urinary Continence With Time" Aust NZ J Obstet Gynaecol, vol. 39, No. 3,

(56) References Cited

OTHER PUBLICATIONS pp. 354-356 (1999) (International Urogynecology Journal and Pelvic Floor Dysfunction, Reprinted from vol. 7, No. 3, pp. 133-137 (1996)).

Petros, P. E. Papa, "New Ambulatory Surgical Methods Using an Anatomical Classification of Urinary Dysfunction Improve Stress, Urge and Abnormal Emptying" Int-Urogynecol-J-Pelvic-Floor-Dysfunct, 8/5, pp. 270-277 1997.

Petros, P. E. Papa, et al., "An analysis of rapid pad testing and the history for the diagnosis of stress incontinence" Acta Obstet Gynecol Scand 71, pp. 529-536 (1992).

Petros, P. E. Papa, et al., "An Anatomical Basis for Success and Failure of Female Incontinence Surgery" Scand J Urol Nephrol, Suppl. No. 153, pp. 55-60 (1993).

Petros, P. E. Papa, et al., "An integral theory of female urinary incontinence—Experimental and clinical considerations" Acta Obstet Gynecol Scand, vol. 69, Suppl. 153, pp. 7-31 (1990), The Scandinavian Association of Obstetricians and Gynecologists.

Petros, P. E. Papa, et al., "Anchoring the midurethra restores bladder-neck anatomy and continence" The Lancet, vol. 354, pp. 997-998 (Sep. 18, 1999).

Petros, P. E. Papa, et al., "Bladder Instability in Women: A Premature Activation of the Micturition Reflex" Neurourology and Urodynamics, vol. 12, pp. 235-238 (1993).

Petros, P. E. Papa, et al., "Cough Transmission Ratio: An Indicator of Suburethral Vaginal Wall Tension Rather Than Urethral Closure?" Acta Obstet Gynecol Scand, vol. 69 Suppl. 153, pp. 37-39 (1990).

Petros, P. E. Papa, et al., "Cure of Stress Incontinence by Repair of External Anal Spincter: Two Case Reports" Acta Obstet Gynecol Scand, vol. 69 Suppl. 153, p. 75 (1990).

Petros, P. E. Papa, et al., "Cure of Urge Incontinence by the Combined Intravaginal Sling and Tuck Operation" Acta Obstet Gynecol Scand, vol. 69 Suppl. 153, pp. 61-62 (1990).

Petros, P. E. Papa, et al., "Further Development of the Intravaginal Slingplasty Procedure—IVS III—(with midline tuck')" Scand J Urol Nephrol, Suppl. 153, pp. 69-71 (1993).

Petros, P. E. Papa, et al., "Non Stress Non Urge Female Urinary Incontinence—Diagnosis and Cure: A Preliminary Report" Acta Obstet Gynecol Scand, vol. 69 Suppl. 153. pp. 69-70 (1990).

Petros, P. E. Papa, et al., "Part I: Theoretical, Morphological, Radiographical Correlations and Clinical Perspective" Scand J Urol Nephrol, Suppl. 153. pp. 5-28 (1993).

Petros, P. E. Papa, et al., "Part II: The Biomechanics of Vaginal Tissue and Supporting Ligaments With Special Relevance to the Pathogenesis of Female Urinary Incontinence" Scand J Urol Nephrol, Suppl. No. 153, pp. 29-40 (1993).

Petros, P. E. Papa, et al., "Part III: Surgical Principles Deriving From the Theory" Scand J Urol Nephrol, Suppl. No. 153, pp. 41-52 (1993).

Petros, P. E. Papa, et al., "Part IV: Surgical Applications of the Theory—Development of the Intravaginal Sling Plasty (IVS) Procedure" Scand J Urol Nephrol, Suppl. No. 153, pp. 53-54 (1993).

Petros, P. E. Papa, et al., "Pregnancy Effects on the Intravaginal Sling Operation" Acta Obstet Gynecol Scand, vol. 69 Suppl. 153, pp. 77-79 (1990).

Petros, P. E. Papa. et al., "The Autogenic Ligament Procedure: A Technique for Planned Formation of an Artificial Neo-Ligament" Acta Obstet Gynecol Scand, vol. 69 Suppl 153, pp. 43-51 (1990).

Petros, P. E. Papa, et al., "The Combined Intravaginal Sling and Tuck Operation. An Ambulatory Procedure for Cure of Stress and Urge Incontinence" Acta Obstet Gynecol Scand, vol. 69 Suppl 153, pp. 53-59 (1990).

Petros, P. E. Papa, et al., "The Development of the Intravaginal Slingplasty Procedure: IVS II—with bilateral 'tucks')", Scand J Urol Nephrol, Suppl. 153. pp. 61-67 (1993).

Petros, P. E. Papa, et al., "The Free Graft Procedure for Cure of the Tethered Vagina Syndrome" Scand J Urol Nephrol, Suppl. No. 153, pp. 85-87 (1993).

Petros, P. E. Papa, et al., "The Further Development of the Intravaginal Slingplasty Procedure: IVS IV—(with "double-breasted" unattached vaginal flap repair and "free" vaginal tapes)" Scand J Urol Nephrol, Suppl. No. 153, pp. 73-79 (1993).

Petros, P. E. Papa, et al., "The Intravaginal Slingplasty Procedure: IVS VI—further development of the 'double-breasted' vaginal flap repair—attached flap" Scand J Urol Nephrol, Suppl. No. 153, pp. 81-84 (1993).

Petros, P. E. Papa, et al., "The Posterior Fornix Syndrome: A Multiple Symptom Complex of Pelvic Pain and Abnormal Urinary Symtoms Deriving From Laxity in the Posterior Fornix of Vagina" Scand J Urol Nephrol, Suppl. No. 153, pp. 89-93 (1993).

Petros, P. E. Papa, et al., "The Role of a Lax Posterior Vaginal Fornix in the Causation of Stress and Urgency Symptoms: A Preliminary Report" Acta Obstet Gynecol Scand, vol. 69 Suppl. 153, pp. 71-73 (1990).

Petros, P. E. Papa, et al., "The Tethered Vagina Syndrome, Post Surgical Incontinence and I-Plasty Operation for Cure" Acta Obstet Gynecol Scand, vol. 69 Suppl. 153, pp. 63-67 (1990).

Petros, P. E. Papa, et al., "The Tuck Procedure: A Simplified Vaginal Repair for Treatment of Female Urinary Incontinence" Acta Obstet Gynecol Scand, vol. 69 Suppl. 153, pp. 41-42 (1990).

Petros, P. E. Papa, et al., "Urethral Pressure Increase on Effort Originates From Within the Urethra, and Continence From Musculovaginal Closure" Neurourology and Urodynamics, vol. 14, pp. 337-350 (1995).

Petros, P. E. Pappa, "Development of Generic Models for Ambulatory Vaginal Surgery—Preliminary Report" International Urogynecology Journal, 9 pages (1998).

Pourdeyhimi, "Porosity of surgical mesh fabrics: New technology", J. Biomed. Mater. Res.: Applied Biomaterials, vol. 23, No. A1, pp. 145-152 (1989), © 1989 John Wiley & Sons, Inc.

Rackley, Raymond R., M.D., et al. "Tension-free Vaginal Tape and Percutaneous Vaginal Tape Sling Procedures" Techniques in Urology, vol. 7, No. 2, pp. 90-100 (2001).

Rackley, Raymond, M.D., "Synthetic slings: Five steps for successful placement" Urology Times, pp. 46, 48-49 (Jun. 2000).

Raz, Shlomo, et al., The Raz Bladder Neck Suspension Results in 206 Patients, The Journal of Urology, pp. 845-850 (Sep. 1992).

Raz, Shlomo, M.D. et al., "Female Urology—Second Edition" University of California at Los Angeles School of Medicine, articles pp. 80-86, 369-381, 382-391, 392-394, 395-398, 435-442, (1996) W.B. Saunders Company.

Raz, Shlomo, M.D., "Modified Bladder Neck Suspension for Female Stress Incontinence" Urology, vol. XVII, No. 1, pp. 82-85 (Jan. 1981) University of California Health Sciences Center, Los Angeles, CA.

Richardson, David A., M.D., et al., "Delayed Reaction to the Dacron Buttress Used in Urethropexy" The Journal of Reproductive Medicine, vol. 29 No. 9, pp. 689-692 (Sep. 1984).

Ridley, John H., M.D., "Appraisal of the Goebell-Frangenheim-Stoeckel sling procedure" Am. J. Obst. & Gynec. vol. 95, No. 5, pp. 714-721 (Jul. 1, 1966).

Roberts, Henry, M.D., M.R.C.O.G., "Cystourethrography in Women" Ethel Bovce University Fellowship vol. 25 No. 293, pp. 253-259 (May 1952) University of Liverpool.

Sloan, W. R., et al., "Stress Incontinence of Urine: A Retrospective Study of the Complications and Late Results of Simple Suprapubic Suburethral Fascial Slings" The Journal of Urology, vol. 110, pp. 533-536 (Nov. 1973).

Spencer, Julia R., et al., "A Comparison of Endoscopic Suspension of the Vesical Neck With Suprapubic Vesicourethropexy for Treatment of Stress Urinary Incontinence" The Journal of Urology, vol. 137, pp. 411-415 (Mar. 1987).

Stamey, Thomas A., M.D., "Endoscopic Suspension of the Vesical Neck for Urinary Incontinence in Females" Ann Surg., vol. 192, No. 4, pp. 465-471 (Oct. 1980).

Stanton, Stuart L., FRCS, FRCOG, "Suprapubic Approaches for Stress Incontinence in Women" JAGS, vol. 38, No. 3, pp. 348-351 (1990), The American Geriatrics Society.

Staskin, David R., et al., "The Gore-tex sling procedure for female sphincteric incontinence: indications, technique, and results" World J Urol., vol. 15, pp. 295-299 (1997) Springer-Verlag.

(56) References Cited

OTHER PUBLICATIONS

Studdiford, William E., M.D., "Transplantation of Abdominal Fascia for the Relief of Urinary Stress Incontinence" Am J Obst Gynec, vol. 47, pp. 764-775 (1944) Bellevue Hospital and New York University College of Medicine.

Ulmsten, U., "Female Urinary Incontinence—A Symptom, Not a Urodynamic Disease. Some Theoretical and Practical Aspects on the Diagnosis and Treatment of Female Urinary Incontinence" The International Urogynecology Journal, vol. 6, pp. 2-3 (1995).

Ulmsten, U., et al., "A Multicenter Study of Tension-Free Vaginal Tape (TVT) for Surgical Treatment of Stress Urinary Incontinence" The International Urogynecology Journal, vol. 9, pp. 210-213 (1998).

Ulmsten, U., et al., "A three-year follow up of tension free vaginal tape for surgical treatment of female stress urinary incontinence" The British Journal of Obstetrics and Gynaecology, vol. 106, pp. 345-350 (Apr. 1999).

Ulmsten, U., et al., "An Ambulatory Surgical Procedure Under Local Anesthesia for Treatment of Female Urinary Incontinence" The International Urogynecology Journal, vol. 7, pp. 81-86 (1996).

Ulmsten, U., et al., "Different Biochemical Composition of Connective Tissue in Continent and Stress Incontinent Women" Acta Obstet Gynecol Scand, vol. 66, pp. 455-457 (1987).

Ulmsten, U., et al., "Intravaginal Slingplasty (IVS): An Ambulatory Surgical Procedure for Treatment of Female Urinary Incontinence" Scand J Urol Nephrol, vol. 29, pp. 75-82 (1995) Scandinavian University Press.

Ulmsten, U., et al., "The unstable female urethra" Am. J. Obstet. Gynecol., vol. 144 No. 1, pp. 93-97 (1982).

Walters, Mark D., Percutaneous Suburethral Slings: State of the Art Presented at the conference of the American Urogynecologic Society, Chicago, 29 pages (Oct. 2001).

Waxman, Steve et al., Advanced Urologic Surgery for Urinary Incontinence, The Female Patient, vol. 21, pp. 93-100 (Mar. 1996).

Webster, George D., "Female Urinary Incontinence" Urologic Surgery—3rd Ed., Ch. 66, pp. 665-679 (1983).

Webster, George D., et al., "Voiding Dysfunction Following Cystourethropexy: Its Evaluation and Management" The Journal of Urology, vol. 144, pp. 670-673 (Sep. 1990) American Urological Association, Inc.

Winter, Chester C., M.D., "Peripubic Urethropexy for Urinary Stress Incontinence in Women" Urology vol. XX, No. 4, pp. 408-411 (Oct. 1982).

Woodside, Jeffrey R., et al., "Suprapubic Endoscopic Vesical Neck Suspension for the Management of Urinary Incontinence in Myelodysplastic Girls" The Journal of Urology, vol. 135, pp. 97-99 (Jan. 1986).

Zacharin, Robert F., "The suspensory mechanism of the female urethra" Journal of Anatomy, vol. 97, Part 3, pp. 423-427, (1963).

Zacharin, Robert F., FRCS, FRCOG, et al, "Pulsion Enterocele: Long-Term Results of an Abdominoperineal Technique" Obstetrics & Gynecology, vol. 55, No. 2, pp. 141-148 (Feb. 1980) The American College of Obstetricians & Gynecologists.

Zimmern, Phillippe E. et al., "Four-Corner Bladder Neck Suspension" Vaginal Surgery for the Urologist, vol. 2, No. 1, pp. 29-36 (Apr. 1994).

Declaration of Johann J. Neisz with Attachment (Mar. 19, 2004).

Bard, "Uretex Polypropylene Urethral Support—Safety, Simplicity, Flexibility" Marketing Material (2002) 8 pages.

Boston Scientific Corp., Boston Scientific Microvasive, "Precision Tack Transvaginal Anchor System—The Precise Approach to Transvaginal Sling Procedures" Marketing Material (1998) 4 pages.

Boston Scientific Corp., Boston Scientific Microvasive, "Precision Twist Transvaginal Anchor System—Low Profile Design for Precise Anchor Placement" Marketing Material (2000) 2 pages.

Boston Scientific Corp., "Advantage A/T—Surgical Mesh Sling Kit" Marketing Material (2002) 1 page.

Boston Scientific Corp., "Precision SpeedTac—Transvaginal Anchor System" Marketing Material (2002) 1 page.

Ethicon, Inc., TVT Tension-free Vaginal Tape, Gynecare, 23 pages (1999).

Gynecare, TVT—"Tension-Free Vaginal Tape, Minimally Invasive, Highly Effective Treatment for Female Stress Urinary Incontinence" Marketing Brochure, Ethicon, Inc. (1999) 6 pages.

Mentor, "The Strength of Suspend" Marketing Material (Mar. 2000) 6 pages.

Mentor, Sabre, "Generation Now" Marketing Material (May 2002) 4 pages.

Mentor, Sabre, Surgical Procedure, Marketing Material (Aug. 2002) 6 pages.

Mentor-Porges, Trans-obturator tape, Le hamac perinial, Nos references, Marketing Material in French language (2003) 1 page.

Porges U.K. Ltd., "Uratape Perineal Hammock Urethral Support Tape—New Generation of Tape Perineal Implantation" Mentor, Marketing Material (2002) 4 pages.

Safyre, "The Essence of a Contemporary Synthetic Sling—Self-Anchoring Complete Adjustability Elastic" Promedon, Marketing Material (Jan. 30, 2002) 4 pages.

Urogynecology, Product Catalog, eg. SIS Technology, Bladder Suspension, Urodynamics and Urinary Diversion, Incontinence, Cook, Urological Inc. (1996) 36 pages.

Dietz, Hans, MD, et al., "Does the tension-free vaginal tape stay where you put it?" Am. J. Obstet Gynecol. V. 188, No. 4, pp. 950-953 (2003).

Drutz, H., et al., "Clinical and Urodynamic Re-evaluation of Combined Abdominal Marlex Sling Operations for Recurrent Stress Urinary Incontinence" Int. Urogynecol J. 1: pp. 70-73 (1990).

Fianu, Stefan, et al, Absorbable Polyglactin Mesh for Retropubic Sling Operations in Female Urinary Stress Incontinence, Gyneol. Obstet. Invest. 16, pp. 45-50 (1983).

Mentor-Porges, Come See Us at Booth #28, Marketing Material (Jul. 2002) 1 page.

Mouly, Patrick, et al., "Vaginal Reconstruction of a Complete Vaginal Prolapse: The Trans Obturator Repair" Journal of Urology, Apr. 2003, vol. 169 (4) supplement, p. 183, Abstract # V 702, AUA (Apr. 26-May 1, 2003) Chicago, IL.

Nicita, G. et al. "Six Year Results of Prosthetic Vaginal Surgery for Cystocele Repair" European Urology Supplements 3 (2004) No. 2, p. 50 (Mar. 24-27 2004).

Ogundipe, Anthony, MD, et al., "Modified Suburethral Sling Procedure for Treatment of Recurrent or Severe Stress Urinary Incontinence" Surg. Gynecol. Obstet., V175, pp. 173-176 (Aug. 1992).

"Safyre and Transobturator", Video file on CD-ROM (2004).

Timmons, M. Chrystie, et al., "Abdominal Sacral Colpopexy in 163 Women with Posthysterectomy Vaginal Vault Prolapse and Enterocele—Evolution of Operative Techniques" J. of Reproductive Medicine, V.35, No. 4, pp. 323-327 (Apr. 1992).

"Vesica Sling Kits with Press-In Percutaneous Anchor System—Simplifying Sling Procedures" Marketing Material, Boston Scientific Corp., Boston Scientific Microvasive, (1998), 4 pages.

Young, Stephen B., et al., "The Mersilene mesh suburethral sling: A clincal and urodynamic evaluation" Am. J. Obstet. Gynecol. V. 173, pp. 1719-1726 (Dec. 1995).

\* cited by examiner

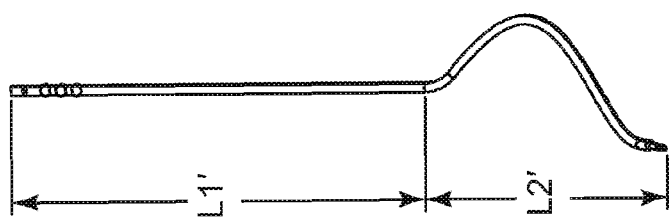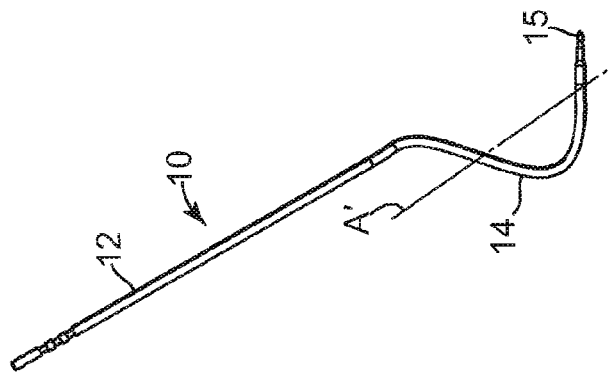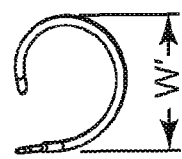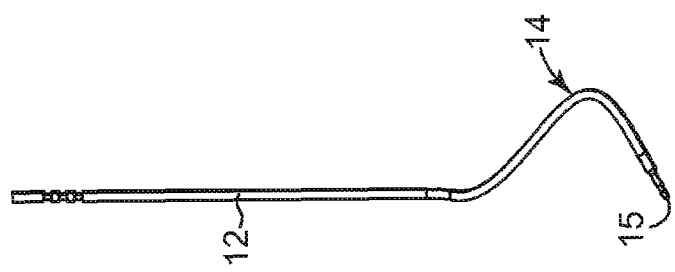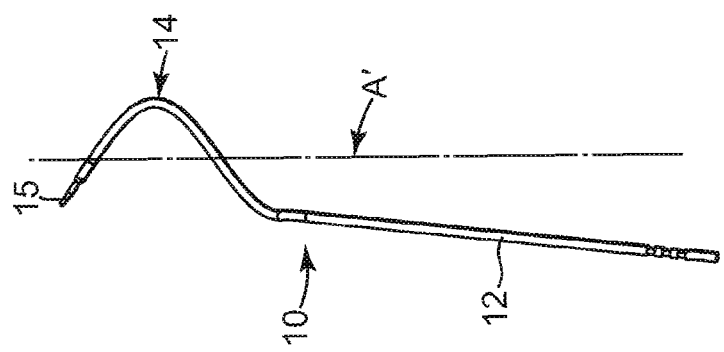

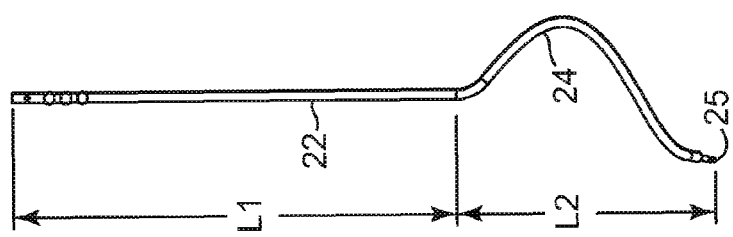
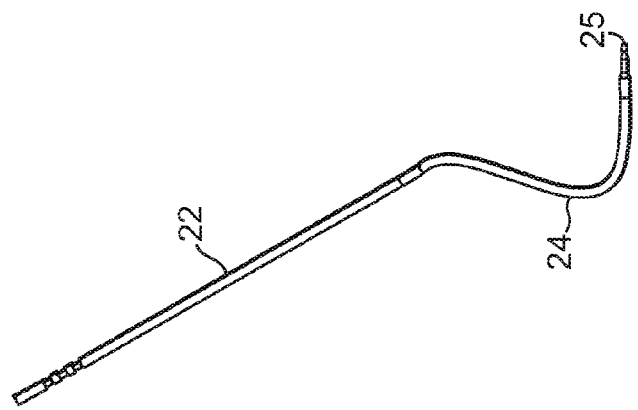
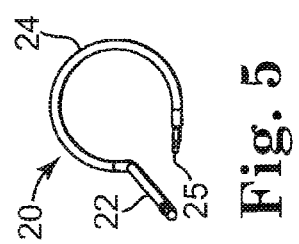
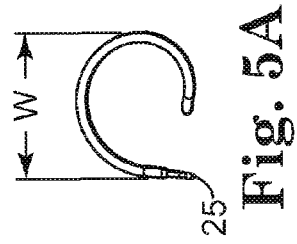
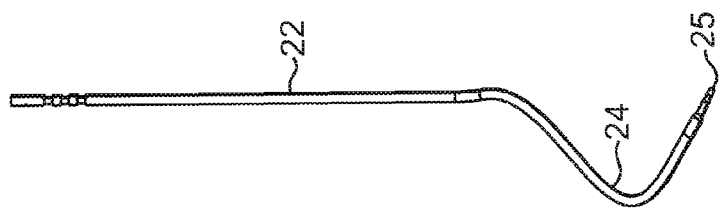
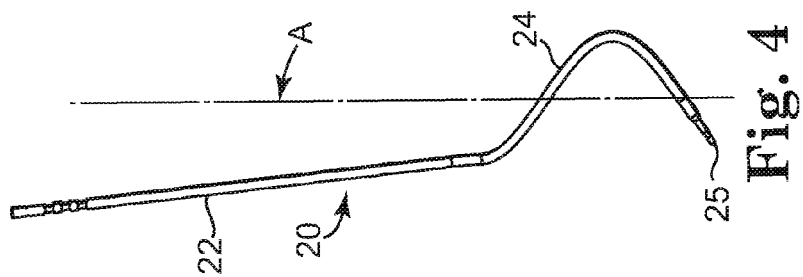

PROLAPSE REPAIR

CROSS-REFERENCE TO RELATED APPLICATIONS

This present application is a continuation of U.S. patent application Ser. No. 12/021,092 filed on Jan. 28, 2008 which is a continuation of U.S. patent application Ser. No. 10/804,718, filed on Mar. 19, 2004, which claims the benefit of U. S. Provisional Patent Application Nos. 60/545,987 filed Feb. 19, 2004 and 60/504,755 filed Sep. 22, 2003 (the entire contents of each are incorporated by reference herein).

BACKGROUND

There are a wide variety of surgical techniques used to repair vaginal prolapse and apical defects. There is no consensus supporting the efficacy of one technique over the others.

Surgical approaches vary. They include vaginal, abdominal and laparoscopic surgical approaches. See Richter K: *Massive Eversion of the Vagina: Pathogenesis, Diagnosis and Therapy of the True Prolapse of the Vaginal Stump*, Clin. Obstet Gynecol 25:897-912 (1982); Diana et al., *Treatment of Vaginal Vault Prolapse with Abdominal Sacral Colpopexy Using Prolene Mesh*, American Journal of Surgery, Vol. 179, (February 2000), Pps. 126-128; Winters et al., *Abdominal Sacral Colpopexy and Abdominal Enterocele Repair in the Management of Vaginal Vault Prolapse*, Urology 56 (Suppl 6A) (2000): 55-63; and Paraiso et al, *Laparoscopic Surgery for Enterocele, Vaginal Apex Prolapse and Rectocele*, Int Urogynecol J (1999), 10:223-229.

Abdominal sacral colpopexy is considered to be an especially efficacious treatment, but it has been criticized for its inability to address posterior wall defects or perineal descent problems. This can result in persistent or altered defactory issues. See Bassler et al., *Abdominal Sacrocolpopexy and Anatomy and Function of the Posterior Compartment*, Obstet. Gyn 2001; 97:678-683. These procedures are generally considered invasive.

Sacrospinous ligament suspensions are also popular. However, these procedures have been criticized for distorting support symmetry about the vaginal axis. This could contribute to a predisposition for future defects in the anterior compartment. See Paraiso et al., *Pelvic support defects and visceral and sexual function in women treated with sacrospinous ligament suspension and pelvic reconstruction*. Am J Obstet Gyn 1996; 175:1423-1431. See also, Guner et al., *Transvaginal Sacrospinous Colpopexy for Marked Uterovaginal and Vault Prolapse*, Inter. J. of Gynec. & Obstetrics, 74 (2001) Pps. 165-170. This fixation is believed to risk complications through damage to the pudendal neurovascular bundle and sciatic nerve. Uterosacral ligament suspension is another repair procedure, but risk of ureteral injury still exists.

PCT Publication No. WO 00/64370 (Gaston) describes a device for treating a prolapse by vaginal suspension. The device comprises an elongate, flexible, pierced material, a suture connected to the material and a suture needle joined to the suture. The device is long enough to enable posterior suspension of the vagina at the promontory (i.e. the front upper part of the sacrum). The other end of the device includes a distal portion having a width such that it can cover at least a large part of the posterior part of the vagina, a rounded cut-out with dimensions that enable it to be engaged around the base of the vagina on at least a large part of the lower half of the wall of the vagina. The suture is connected to the article so that it is offset sidewise in relation to the cut-out.

PCT Publication No. WO 00/27304 (ORY et al.) discloses a suspension device for treating prolapse and urinary incontinence. The device comprises at least one filiform suspension cord with limited elasticity and at least two anchoring parts linked to the ends of the cord.

PCT Publication No. WO 02/078552-A1 discloses an apparatus for treating vaginal vault disorders.

Published U.S. Pat. Appl. Nos. 2003/0220538-A1 and 2003/0176762 purport to disclose surgical instruments for treating prolapse.

U.S. Pat. No. 5,112,344 and PCT Publication No. PCT/US02/32284 disclose surgical devices for female pelvic health procedures. The IVS Tunneller device is available from U.S. Surgical of Norwalk, Conn. The IVS device comprises a fixed delta wing handle, a hollow metal tube and a stylet that is placeable within the tube. The stylet has a rounded plastic tip on one end and an eyelet at the other end. The device may be used to implant a polypropylene tape for infracoccygeal sacropexy and other surgical procedures. See Farnsworth, *Posterior Intravaginal Slingplasty (Infracoccygeal Sacropexy) For Severe Posthysterectomy Vaginal Vault Prolapse—A Preliminary Report on Safety and Efficacy*, Int. Urogynecol. J. (2002) 13:4-8; Petros, *Vault Prolapse II: Restoration of Dynamic Vaginal Supports by Infracoccygeal Sacropexy, an Axial Day-Case Vaginal Procedure*, Int Urogynecol J (2001) 12:296-303; and Petros, *The Intravaginal Slingplasty Operation, a Minimally Invasive Technique for Cure of Urinary Incontinence in the Female*, Aust. NZ J Obstet Gynaecol, (1996); 36: 4:453.

A single, rigid, hollow metal tube is associated with the IVS Tunneller device. This single tube passes through two separate regions of the patient's body with the attendant risk of cross contamination. The outer diameter of the tube is also relatively large (about 0.25 inches) with the attendant risk of tissue damage due to a large diameter needle.

The polypropylene tape supplied with the IVS Tunneller is a thin, rectangular shape, believed to be approximately 8 mm×350 mm. The thin, rectangular tape supplied with the IVS Tunneller is not believed to be extensible. Under a longitudinal force, the implant is highly resistant to elongation. It is believed that inextensible polypropylene tapes may be apt to exhibit a greater association with erosion and failure.

A recent abstract describes using a 15×14 cm implant, placed transvaginally, to repair the anterior, median perineal defect. See Mouly et al., *Vaginal Reconstruction of a Complete Vaginal Prolapse: The Trans Obturator Repair*, Journal of Urology, April 2003, Vol 169 (4) supplement, p 183, Abstract #V 702, AUA Apr. 26-May 1, 2003, Chicago, Ill. The abstract also discloses that wings of the mesh are inserted through the obturator holes. Another publication describes an anterior wall repair. See Salomon et al., *Treatment of Anterior Vaginal Wall Prolapse with Porcine Skin Collagen Implant by the Transobturator Route: Preliminary Results*; European Urology 45 (2004), 219-245. This procedure utilizes an Emmet needle to pierce the obturator foramen.

BRIEF SUMMARY

The present invention is directed to novel surgical instruments for surgical procedures that treat prolapse. Novel surgical procedures that utilize such instruments are also disclosed.

In one aspect, the present invention comprises a surgical instrument for inserting an implant for treating female prolapse. The surgical instrument comprises a handle and a needle portion. The needle portion has a straight portion emerging from the handle and a generally helical portion having a distal end region. The needle portion is sized and shaped so that the distal end region may initially be moved through a patient's obturator foramen toward the region of the patient's ischial spine, and then toward a vaginal incision in the region of the vaginal apex, so that an implant may be received by the distal end of the needle and moved from the vaginal incision through the patient's obturator foramen.

The helical portion may comprise either a left or a right handed helical portion. Preferably, the needle portion has a generally circular cross section with a diameter of less than about 5.5 mm and more than about 0.5 mm In a preferred embodiment, the straight portion of the instrument has a longitudinal axis and the helical portion has a length, measured along the longitudinal axis of the straight portion, of more than 2 inches and less than twelve inches. In the preferred embodiment, the helical portion has a width of more than about 1 inch and less than about 9 inches. Preferably, the helical portion has a pitch of at least 2 inches and less than seven inches and a radius of at least 0.5 inches and less than four inches.

In a preferred embodiment, the straight portion of the instrument has a longitudinal axis and the helical portion has an axis that is not parallel to the axis of the straight portion. The axis of the straight portion and the axis of the helical portion form an angle, preferably of about 8 degrees. The distal end portion of the instrument points away from the handle and at an acute angle relative to a plane that is perpendicular to the longitudinal axis of the straight portion of the instrument.

In another aspect, the present invention comprises an assembly of surgical instruments for treating female prolapse. The assembly comprises a first surgical instrument comprising a handle; a needle portion having a straight portion emerging from the handle and a generally right handed helical portion having a distal end region. The needle portion is sized and shaped so that the distal end region may initially be moved through a patient's obturator foramen toward the region of the patient's ischial spine, and then toward a vaginal incision in the region of the vaginal apex. The assembly includes a second surgical instrument comprising a handle; a needle portion having a straight portion emerging from the handle and a generally left handed helical portion having a distal end region. The needle portion of the second needle is sized and shaped so that the distal end region may initially be moved through a patient's obturator foramen toward the region of the patient's ischial spine, and then toward a vaginal incision in the region of the vaginal apex. The assembly also includes an implant for treating the prolapse.

In a preferred embodiment, the assembly may include a pair of dilating connectors and insertion sleeves surrounding the implant. Alternatively the distal end portions of the needles may include eyelets. The implant may be extensible or inextensible. Preferably, an insertion sleeve accompanies an extensible implant.

A surgical procedure is also described. The surgical procedure can include the steps of: i) providing a first surgical instrument comprising a handle, a needle portion having a straight portion emerging from the handle and a generally right handed helical portion having a distal end region; a second surgical instrument comprising a handle, a needle portion having a straight portion emerging from the handle and a generally left handed helical portion having a distal end region; ii) creating a vaginal incision; iii) incising the patient's skin in the region of the patient's obturator foramen on a first side of the patient, iv) passing the distal end portion of the first surgical instrument through the obturator foramen and then through the vaginal incision; v) associating the implant with the first surgical instrument; vi) incising the patient's skin in the region of the patient's obturator foramen on a second side of the patient, vii) passing the distal end portion of the second surgical instrument through the obturator foramen and then through the vaginal incision; viii) associating the implant with the second surgical instrument; ix) moving the distal end portion of the first surgical instrument from the vaginal incision through the patient's obturator foramen with an end of the implant associated with the distal end portion; x) moving the distal end portion of the second surgical instrument from the vaginal incision through the patient's obturator foramen with an end of the implant associated with the distal end portion; and xi) attaching the implant to the vagina. Preferably, the step of creating a vaginal incision includes the step of creating a vaginal incision in a region of the apex of the vagina. Also preferably, the step of passing the distal end portion of the first surgical instrument through the obturator foramen and then through the vaginal incision includes the step of passing the distal end of the instrument through the inferior part of the obturator membrane in the region of the obturator foramen above the ischiopubic ramus.

BRIEF DESCRIPTION OF THE DRAWINGS

Other features and advantages of the present invention will be seen as the following description of particular embodiments progresses in conjunction with the drawings, in which:

FIG. 1 is a top view of a surgical instrument showing an axis for a helical portion of the instrument;

FIG. 1A is another view of the surgical instrument of FIG. 1;

FIG. 2 is an end view of the surgical instrument of FIG. 1, taken in a plane substantially perpendicular to the axis of the helical portion of the instrument;

FIG. 2A is a view of the instrument of FIG. 1 taken in a plane substantially perpendicular to the axis of a straight portion of the instrument;

FIG. 3 is another view of the instrument of FIG. 1;

FIG. 3A is another view of the instrument of FIG. 1;

FIG. 4 is a top view of a surgical instrument showing an axis for a helical portion of the instrument;

FIG. 4A is another view of the surgical instrument of FIG. 4;

FIG. 5 is an end view of the surgical instrument of FIG. 4, taken in a plane substantially perpendicular to the axis of the helical portion of the instrument;

FIG. 5A is a view of the instrument of FIG. 4 taken in a plane substantially perpendicular to the axis of a straight portion of the instrument;

FIG. 6 is another view of the instrument of FIG. 4;

FIG. 6A is another view of the instrument of FIG. 4;

FIGS. 9 through 22 schematically illustrate the use of the assembly of surgical articles of FIG. 8 in treating prolapse, wherein:

FIG. 9 shows a surgical instrument just as it begins to traverse the patient's right obturator foramen;

FIG. 10 illustrates the distal end portion of a surgical instrument after it has traversed the obturator foramen and while it is being moved in the general direction of the ischial spine;

FIG. 11 illustrates the distal end portion of the surgical instrument as it is being moved toward a vaginal incision and a surgeon's finger;

FIG. 12 illustrates the surgical needle after the distal end region has entered the vaginal vault;

FIG. 13 illustrates a connecting dilator and a portion of an implant assembly as the connecting dilator is being moved toward the distal end region of the surgical instrument;

FIG. 14 illustrates the connecting dilator after it has been connected to the distal end region of the surgical instrument;

FIG. 15 illustrates the implant assembly after one end portion has been guided by the surgical instrument through a vaginal incision, through tissue and then toward an incision adjacent the obturator foramen;

FIG. 16 illustrates the end portion of the implant assembly after it has traversed the obturator foramen and emerged from a skin incision;

FIG. 17 illustrates a scissors after it has separated the surgical instrument and dilating connector from the remaining portion of the implant assembly;

FIG. 18 illustrates a second surgical instrument after it has passed through the patient's left obturator foramen, and after the distal end region of the surgical instrument has emerged through a vaginal incision, which figure also illustrates a second dilating connector attached to the distal end region of the second needle;

FIG. 19 illustrates the implant assembly after the surgical instrument has guided the dilating connector through the patient's left obturator foramen;

FIG. 20 illustrates a surgical scissors being used to separate the dilating connector (with attached surgical instrument) from the rest of the implant assembly;

FIG. 21 illustrates insertion sheaths of the implant assembly being removed from the body; and FIG. 22 illustrates the implant that corrects the vaginal prolapse just prior to it being trimmed to the skin incisions adjacent the patient's obturator foramen.

DETAILED DESCRIPTION

Figure 7:
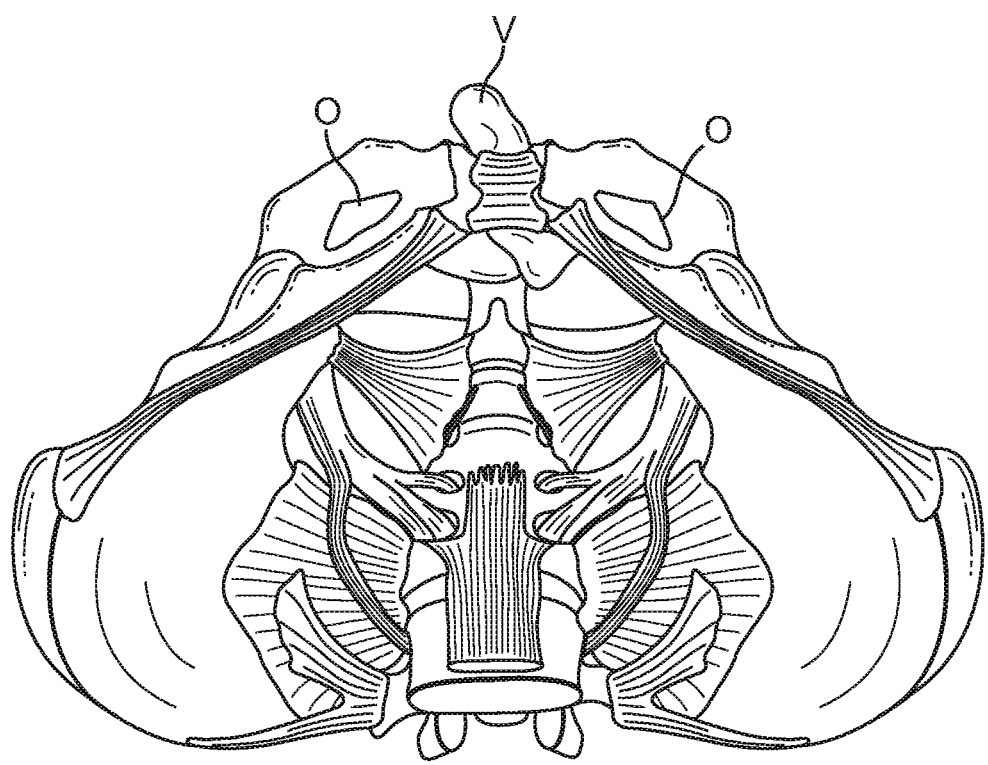
FIG. 7 is a schematic view of portions of a human female pelvic region, showing a prolapsed vagina.

The following description is meant to be illustrative only and not limiting. Other embodiments of this invention will be apparent to those of ordinary skill in the art in view of this description.

FIGS. 1-3A illustrate a surgical instrument for use on one side of the patient's body. FIGS. 4-6A disclose a surgical instrument for use on the opposite side of the patient's body.

The surgical instrument 10 includes a straight portion 12, a helical portion 14, and a distal end region 15. Similarly, the surgical instrument 20 includes a straight portion 22, a helical portion 24, and a distal end region 25. Preferably, the surgical instruments 10 and 20 include handles 11 and 21 (FIG. 8) which are not shown in FIGS. 1-6A.

The surgical instruments 10 and 20 are adapted for a surgical procedure for reconstruction of the vaginal vault, as described more fully below. The cross sectional shape of the straight and helical portions can be of a wide variety of shapes and is preferably small. For a circular cross section, the diameter is preferably less than about 5.5 mm and more than about 0.5 mm.

As an example, not intended to be limiting, the surgical instrument 10 may have a diameter of 0.125 inches. The length L1' is preferably more than about 5 inches and may be about 6 inches, the length L2' is preferably more than 1 inch, more preferably more than 2 inches and even more preferably about 2.76 inches. The length L1' is preferably less than twelve (12) inches. The width W' is preferably more than one inch and less than about 9 inches. In a preferred embodiment the width W' may be about 2.15 inches. Preferably about two inches of the straight portion 12 project from the end of the handle 11. The helical portion 14 preferably has a radius of at least 0.5 inches, more preferably 0.825 inches and a pitch of at least about 2 inches preferably about 3.65 inches. The surgical instrument may be formed about a mandrel with a diameter of 1.5 inches and a groove (for receiving the surgical instrument) with a pitch of 3 inches. Notably, the axis A' of the helical portion 14 is offset from the longitudinal axis of the straight portion 12 (see FIGS. 1 and 3). In this embodiment, the offset is about 8 degrees. In a preferred embodiment, the offset for both instruments 10 and 20 is the same and at least 5 degrees. The bend between the straight and helical portions 12 and 14 may have a radius of about 0.3 inches.

Preferably, the distal end portion 15 of the surgical instrument points away from the handle 11 (FIG. 8) and at an acute angle relative to a plane that is perpendicular to the longitudinal axis of the straight portion 12 of the instrument.

Similarly, for instrument 20, length L1 may be about 6 inches, the length L2 is about 2.76 inches, and width W of about 2.15 inches. Preferably about two inches of the straight portion 22 project from the end of the handle 21. Again, the axis A of the helical portion 24 is offset from the longitudinal axis of the straight portion 22. The helical portion 24 preferably has a radius of 0.825 inches and a pitch of about 3.65 inches. The ranges for the size and shape of the instrument 20 are the same as described above for the instrument 10.

One of the helical portions 14 and 24 has a right hand helix and the other has a left hand helix. The surgical instruments 10 and 20 may be constructed from any suitable polymeric or metallic material. One suitable material is stainless steel 17-4 PH hardened to H900.

Figure 8:
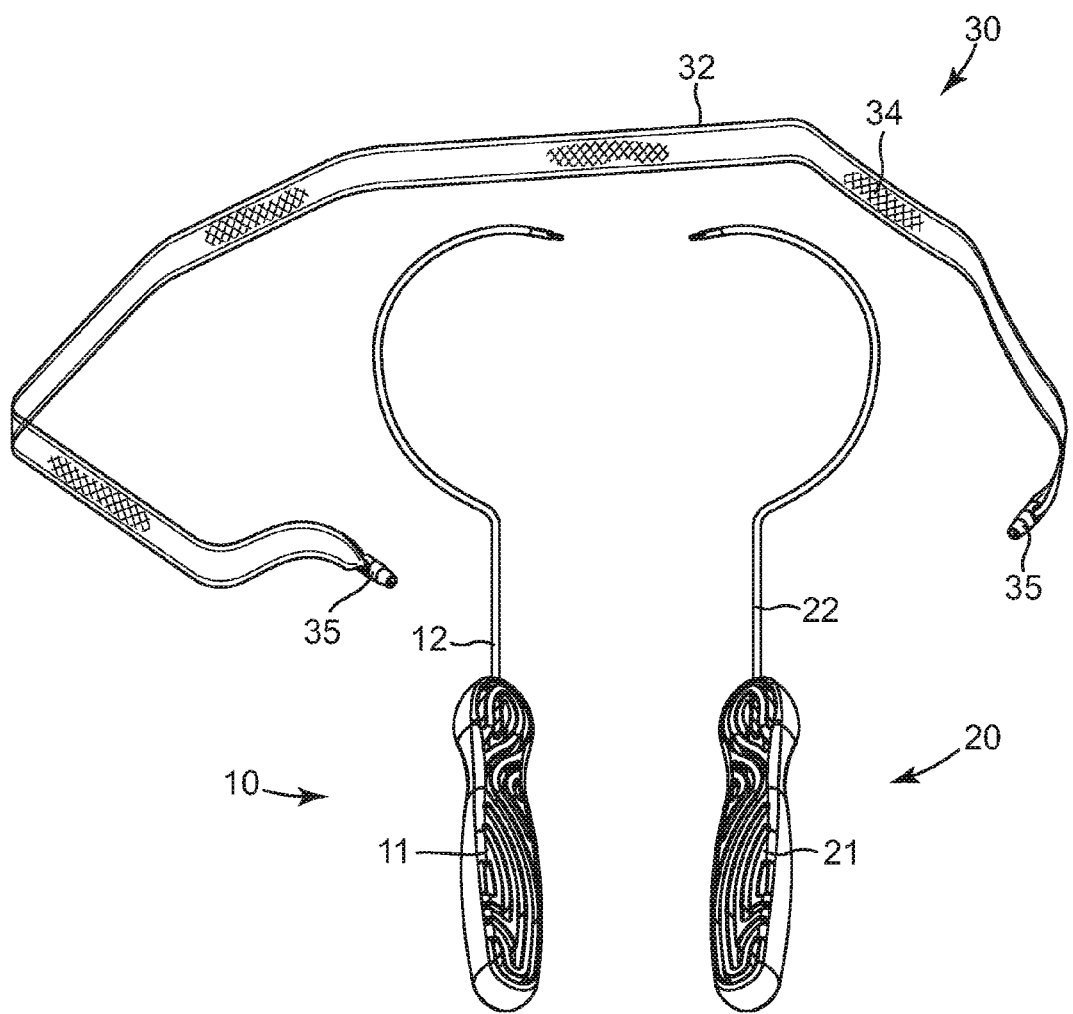
FIG. 8 is a perspective view of an assembly of surgical articles for use in a subsequent procedure for treating prolapse.

FIG. 8 shows an assembly of surgical articles 10, 20 and 30 for treating prolapse. The assembly preferably includes surgical articles 10 and 20 and an implant assembly 30 with dilating connectors 35, implant 34 and separable insertion sheath 32. The dilators and insertions sheath are optional. Alternatively, for example, the distal end portions of the surgical instruments 10 and 20 may include eyelets for receiving the implant 34.

The distal end regions 15 and 25 may have surfaces that are specially shaped to engage complementary surfaces on the dilating connectors 35 of an implant assembly 30. Such assemblies are disclosed in published U.S. Pat. Application Nos. 2003/0171644-A1 and 2003/0176875-A1.

The implant assemblies 30 typically include an implantable material 34 that remains in the body. The implantable material may comprise synthetic or non-synthetic materials or hybrids, composites or combinations thereof.

A synthetic material is preferable. Suitably synthetic materials include polymerics, and plastics and any combination of such materials. Commercial examples of such materials include Mersile™, Teflon™, Gore-Tex™, Silastic™, Marlex™, Prolene™, and Vaskutek™. Other examples of suitable materials include those disclosed in U.S. Pat. No. 6,652,450. Specific examples of synthetic sling materials include absorbable and non-absorbable materials such as polypropylene, polyethylene, nylon, PLLA and PGA. Additional meshes are disclosed in Dietz et al., *Mechanical Properties of Urogynecologic Implant Materials*, Int. Urogynecol. J. (2003) 14: 239-243; and Iglesia et al., *The Use of Mesh in Gynecologic Surgery*, Int. Urogynecol. J. (1997) 8:105-115.

Possible non-synthetic materials include allografts, homografts, heterografts, autologous tissues, cadaveric fascia and fascia lata.

Surgical Methods

In another aspect, the present invention comprises a surgical method, e.g. for prolapse repair. FIG. 7 shows a prolapsed vagina V and a female pelvis with obturator foramen O.

FIGS. 9 through 22 illustrate one example of a surgical procedure for treating prolapse. The goal of the procedure is to perform a vaginal vault suspension using an implant fixed relative to the vagina (e.g. on or near the vaginal apex). FIG. 8 shows surgical instruments 10 and 20 and implant assembly 30 that are conveniently assembled for purposes of conducting the subsequent surgery. The surgical instruments 10 and 20 and implant assembly 30 may optionally be packaged together and opened just prior to the procedure. The implant assembly 30 preferably includes an implantable surgical mesh 34, a separable insertion sleeve 32 and a pair of dilating connectors 35.

For fitting the implant 34, at least two routes are possible: one with an anterior dissection and one with posterior dissection. This procedure can be conducted after previous or concomitant hysterectomy and in cases of uterus preservation. Preferably, specific instruments 10 and 20 are passed through the membrane OM in the region of the obturator foramen O to place the implant 34. The implant 34 stabilizes the vaginal vault by fixation on both sides through, e.g. pelvic muscles and membranes.

Posterior Route Fixation

The posterior vaginal wall is incised longitudinally from the apex AP down to the perineum incision. (Lowest part incision may be done for posterior myorraphy). The rectum is dissected from the vaginal wall, preferably substantially the entire portion. The para-rectal space is opened in both sides with dissection deeply to the ischial spines IS. The index finger of the surgeon can palpate levator ani and deeper, the ischial spine IS.

Figure 9:
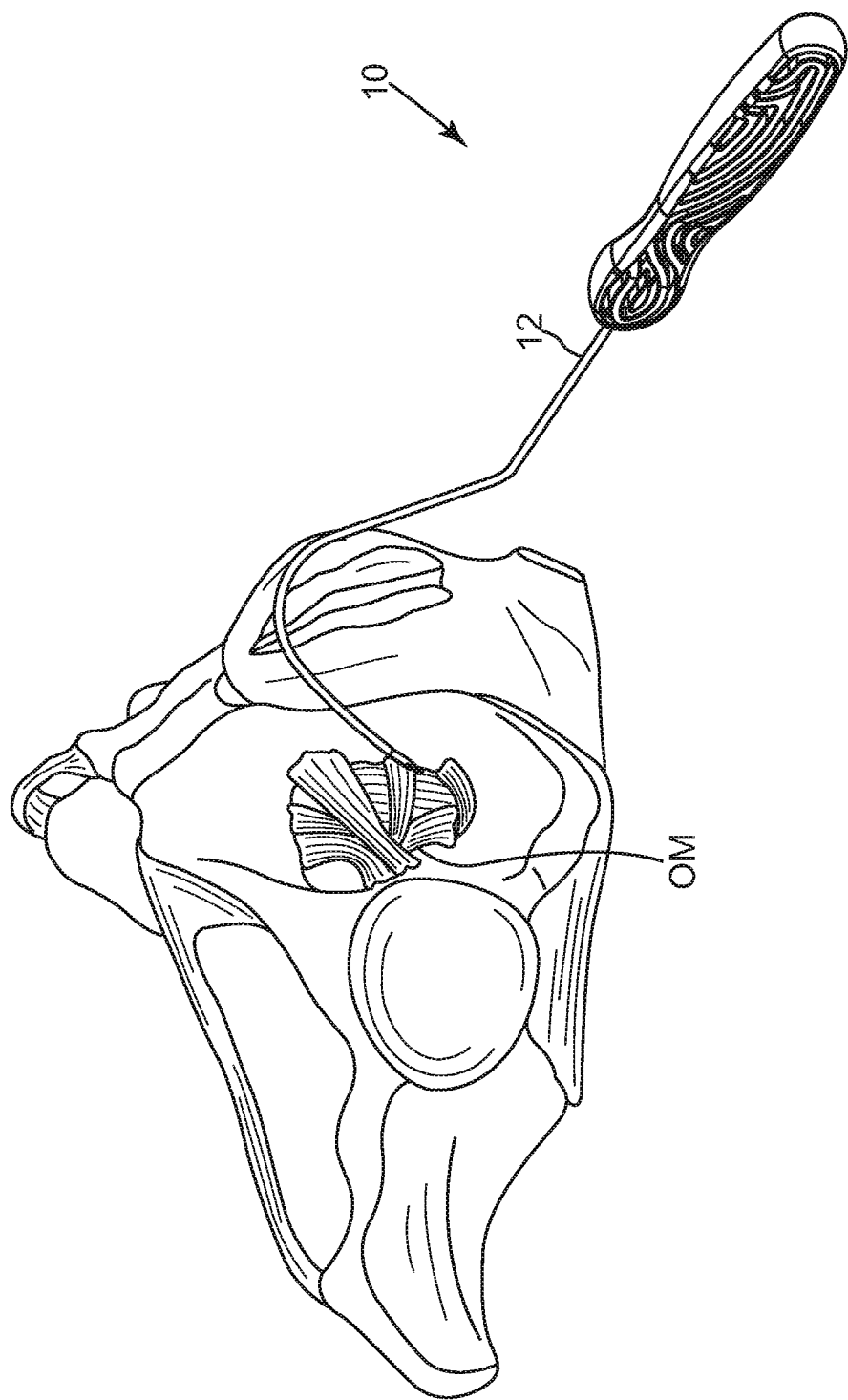
Figure 10:
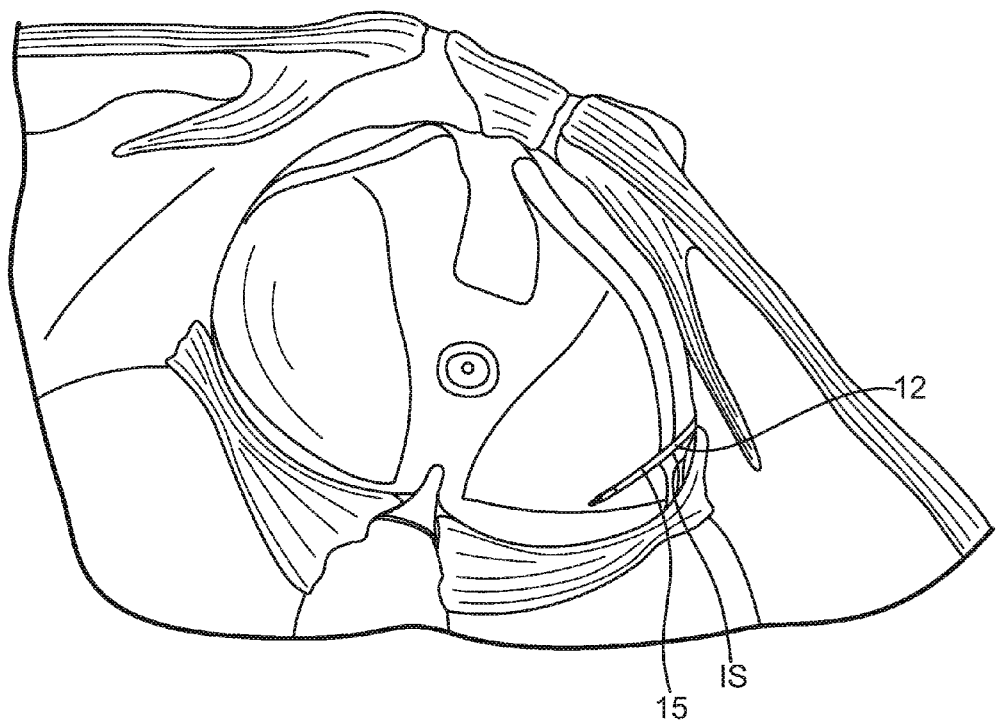
Figure 11:
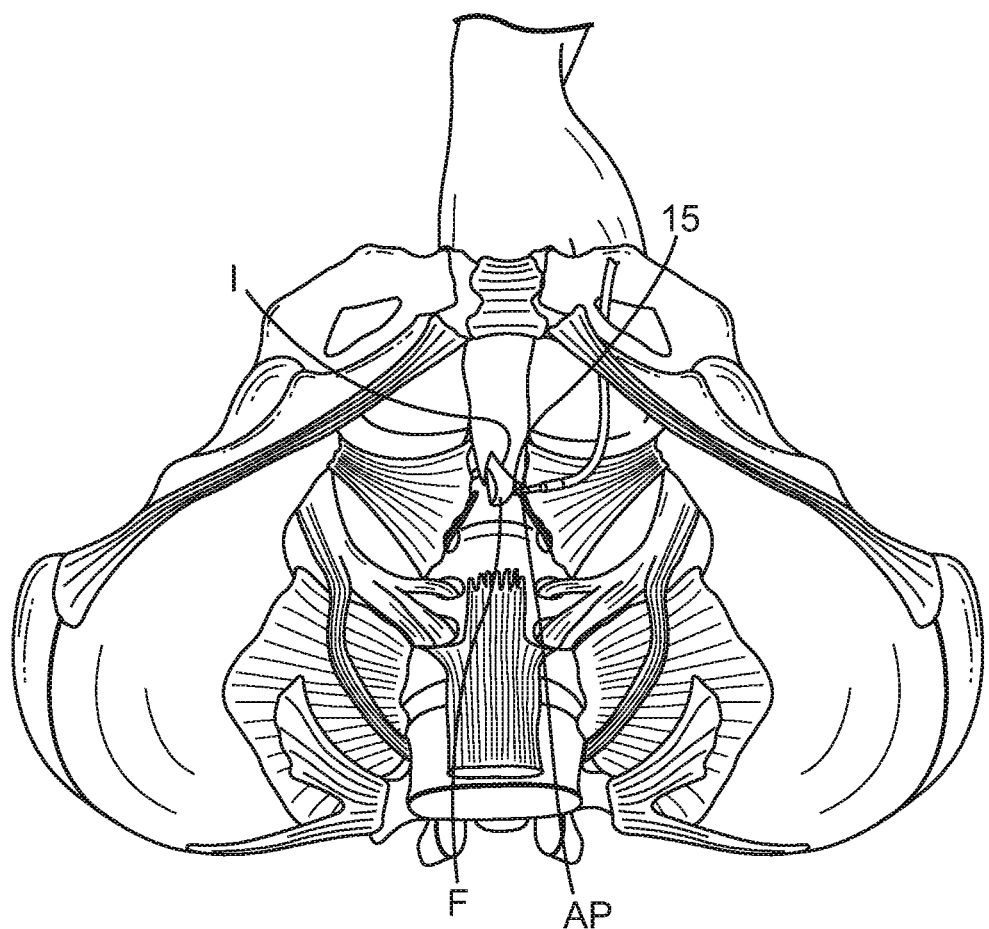
Figure 12:
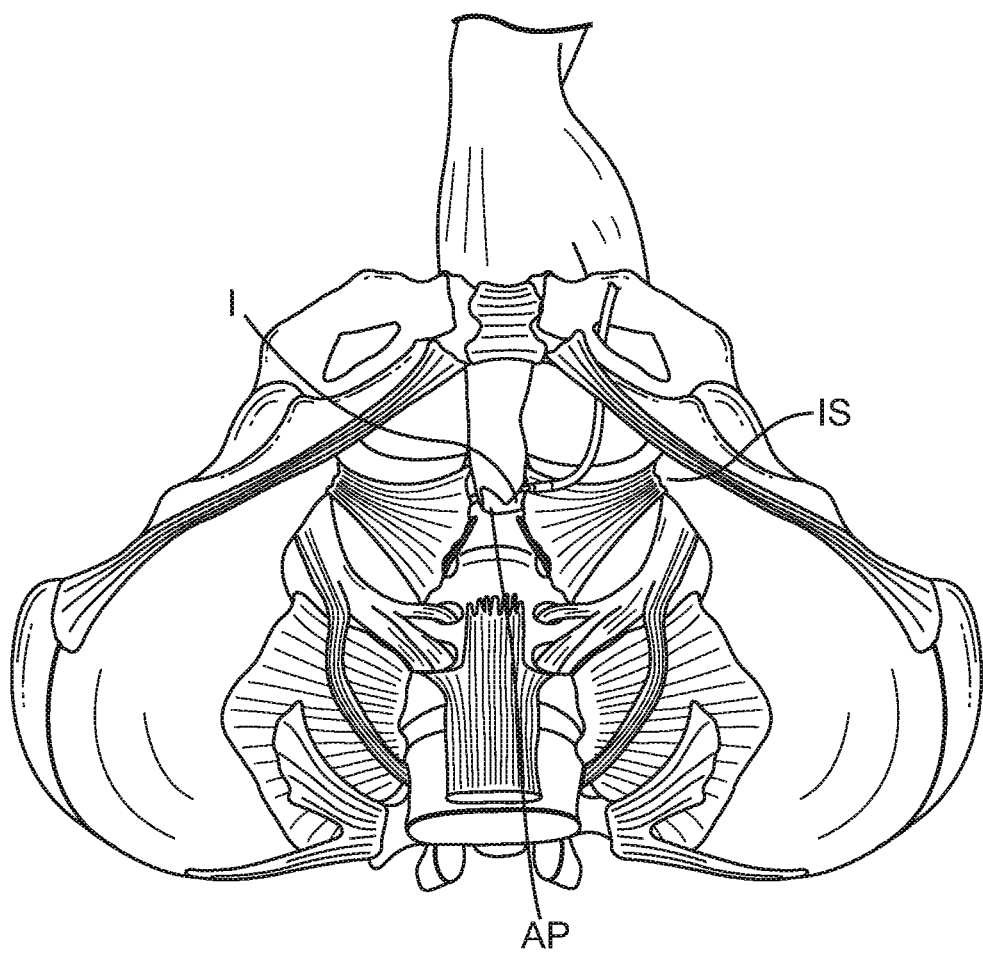

FIG. 9 schematically illustrates a preferred needle passage. The needle passage is preferably through the inferior part of the obturator membrane O in the region of the obturator foramen above the ischio-pubic ramus. After a small skin incision, the distal end portion 15 of the instrument 10 is pushed through the obturator membrane O. As shown in FIG. 10, the distal end portion 15 is moved initially toward the region of the patient's ischial spine IS. The surgeon's index finger can palpate the needle tip through the muscular wall going to the ischial spine IS. The distal end 15 of the instrument is pushing out through the levator ani when it arrives at the level of the spine. FIG. 11 shows the surgeon's finger palpating the distal end 15 of the needle. FIG. 12 shows the arrangement after the distal end portion of the needle after it has passed through a vaginal incision I.

Figure 13:
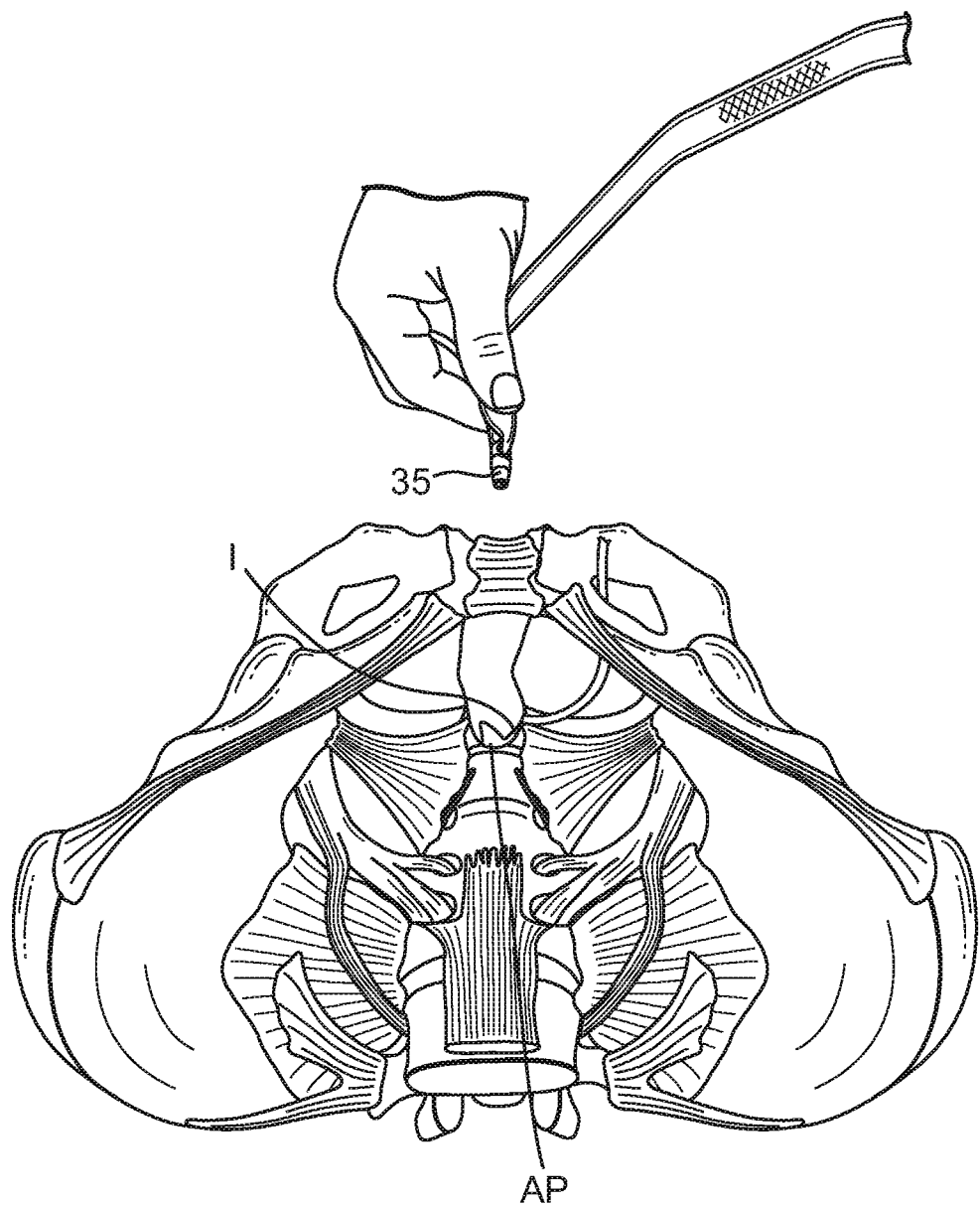
Figure 14:
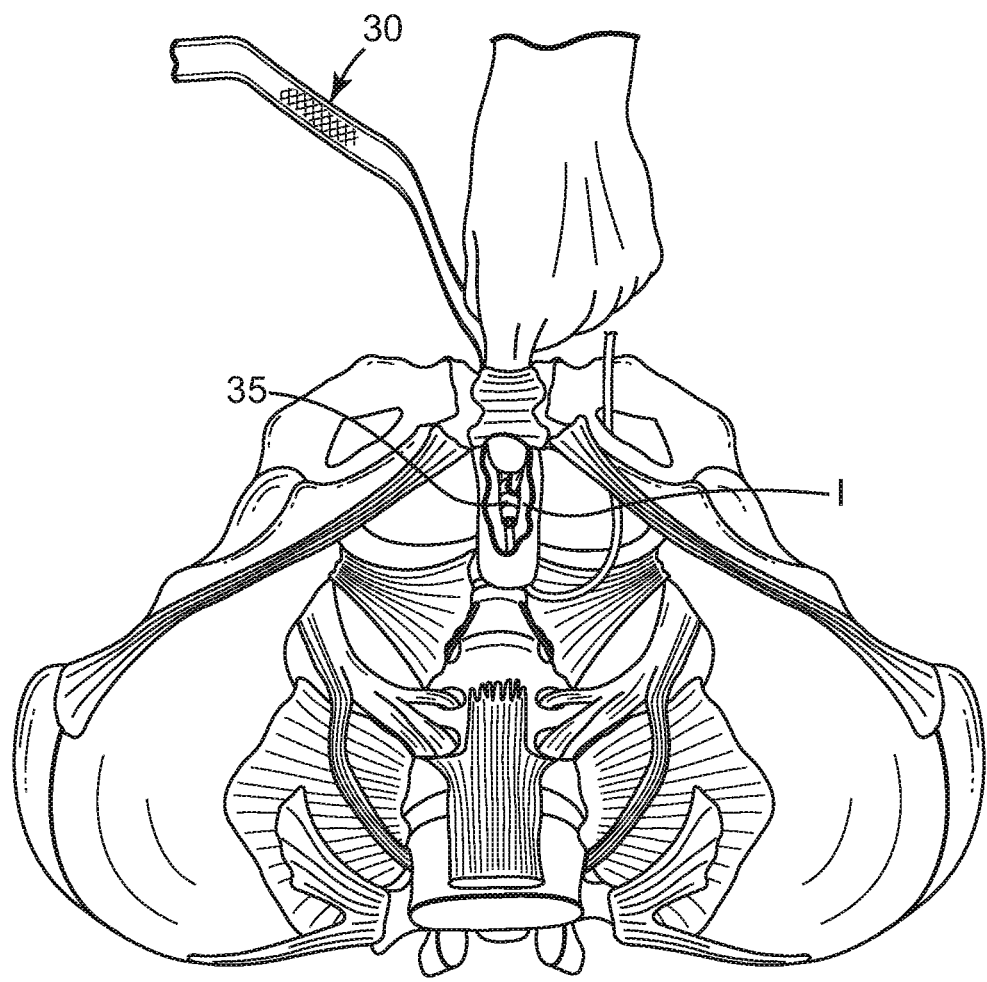
Figure 15:
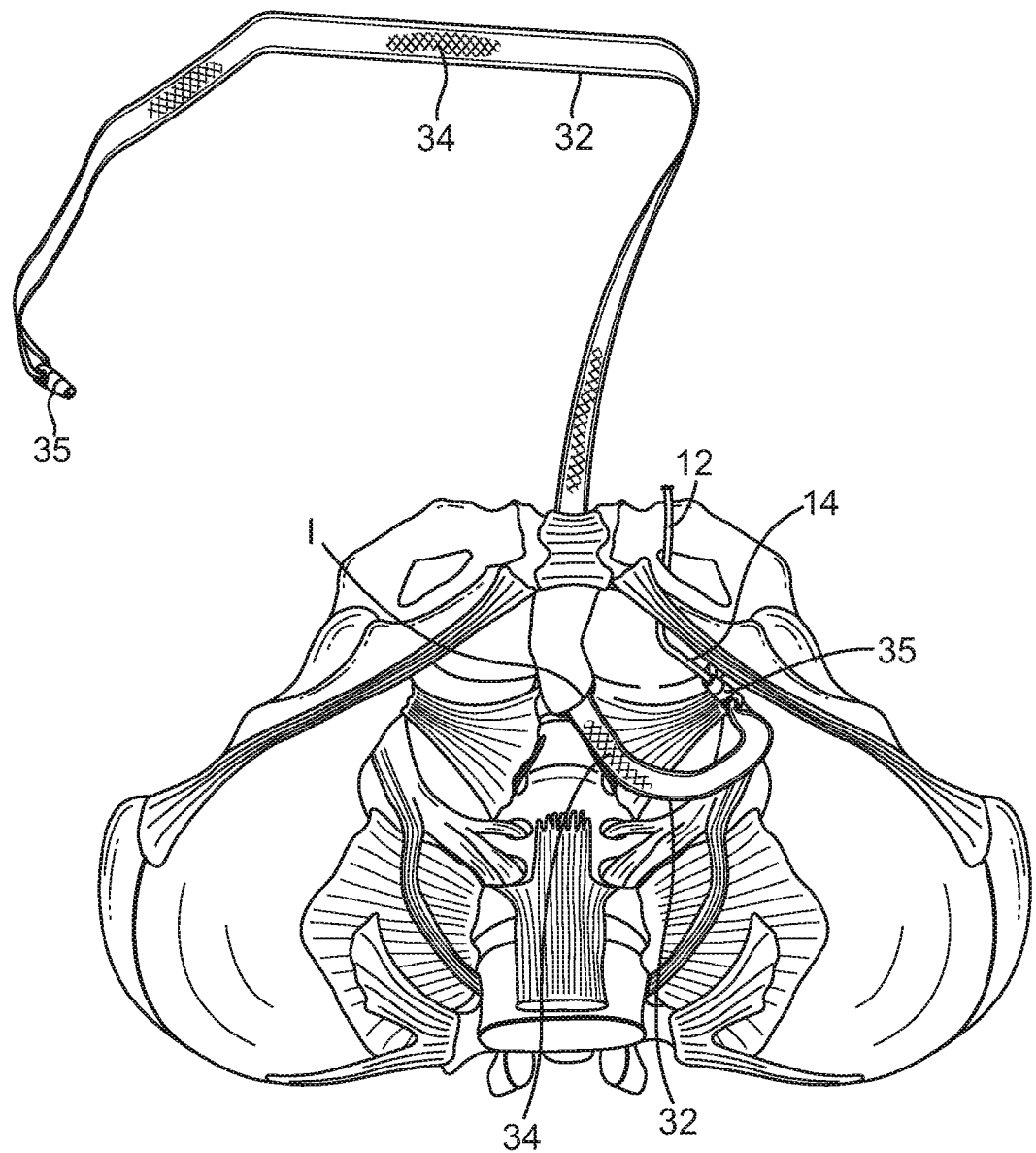
Figure 16:
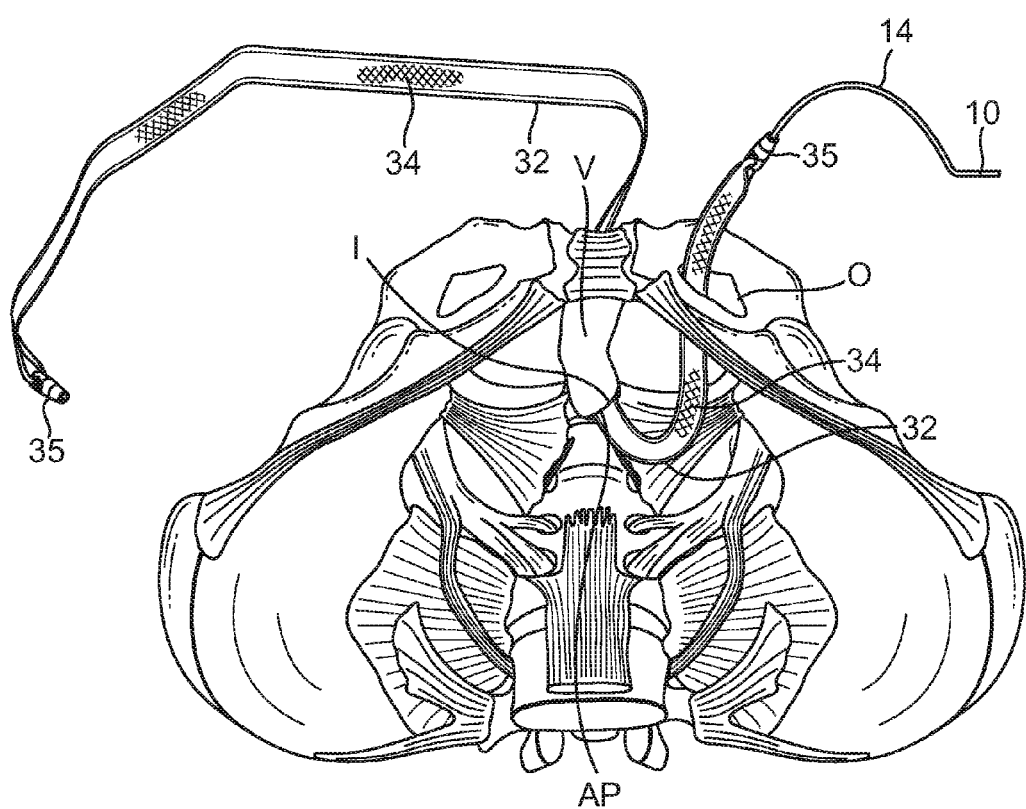
Figure 17:
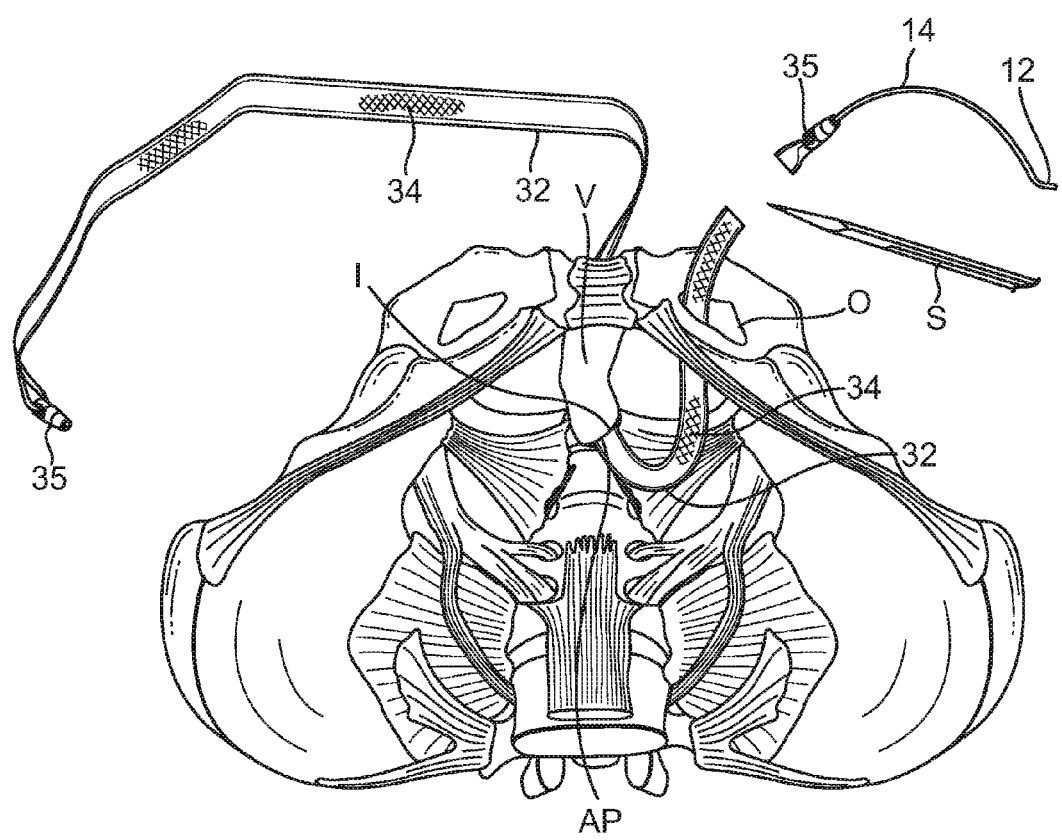

In FIG. 13, the surgeon moves the dilating connector 35 of the implant assembly 30 toward the end portion 15 of the needle. The dilating connector 35 is then connected to the needle tip (FIG. 14). This is shown taking place within the vaginal region. Preparation for this step is shown in FIG. 13. As shown in FIGS. 15 and 16, the needle 12 is pulled back out obturator O and the implant assembly 30 is essentially in place on one side of the patient. FIG. 17 illustrates a scissors S after it has separated the surgical instrument 10 and dilating connector 35 from the remaining portion of the implant assembly 30.

Figure 18:
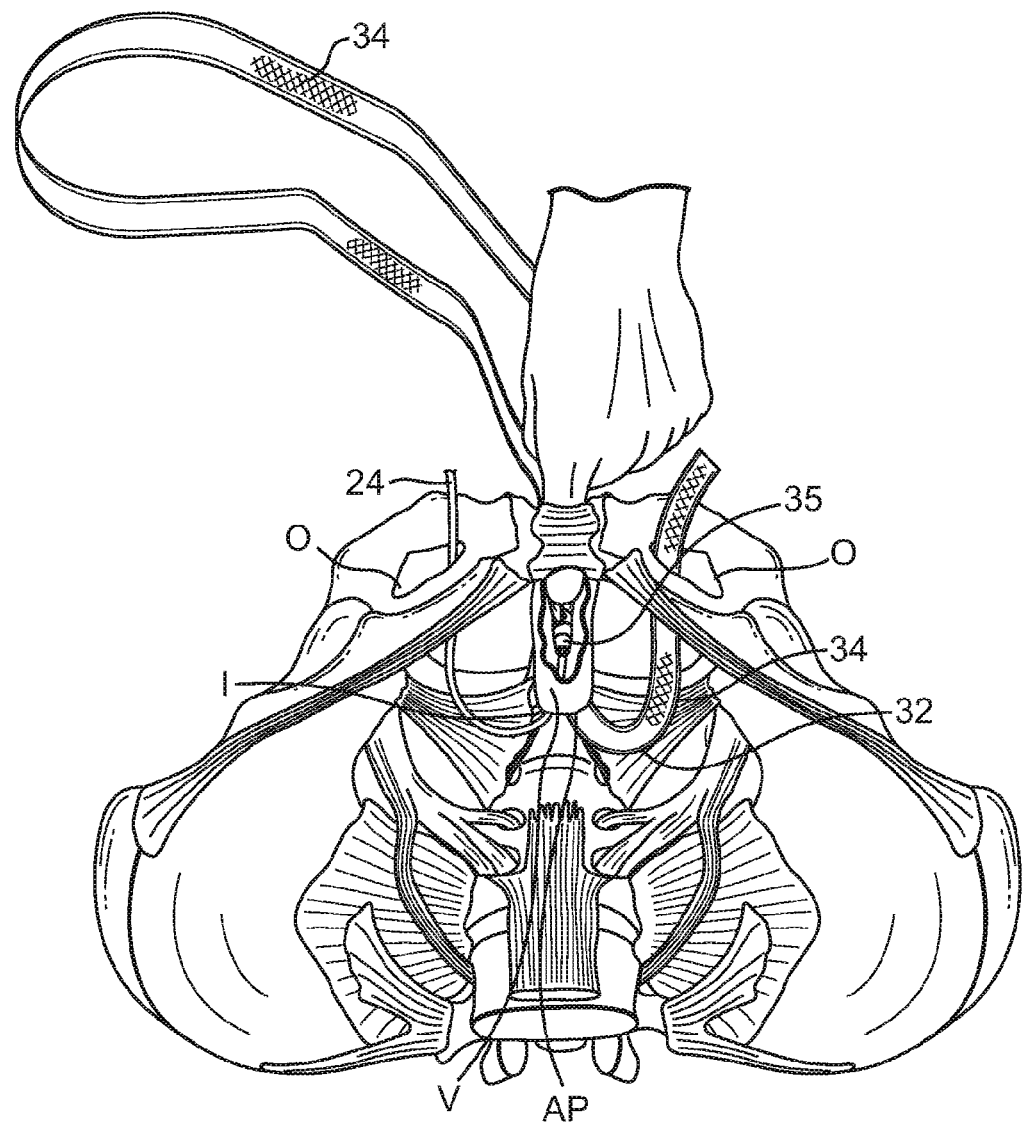
Figure 19:
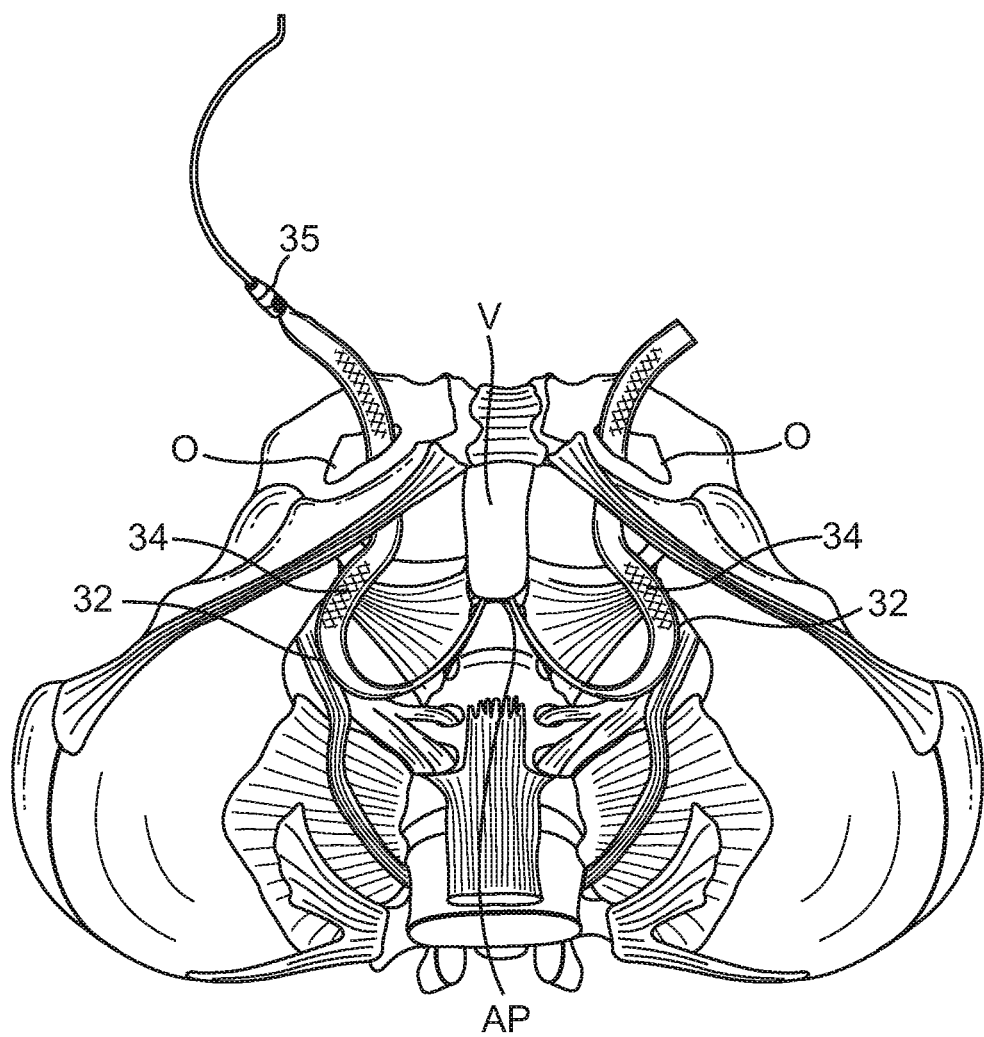
Figure 20:
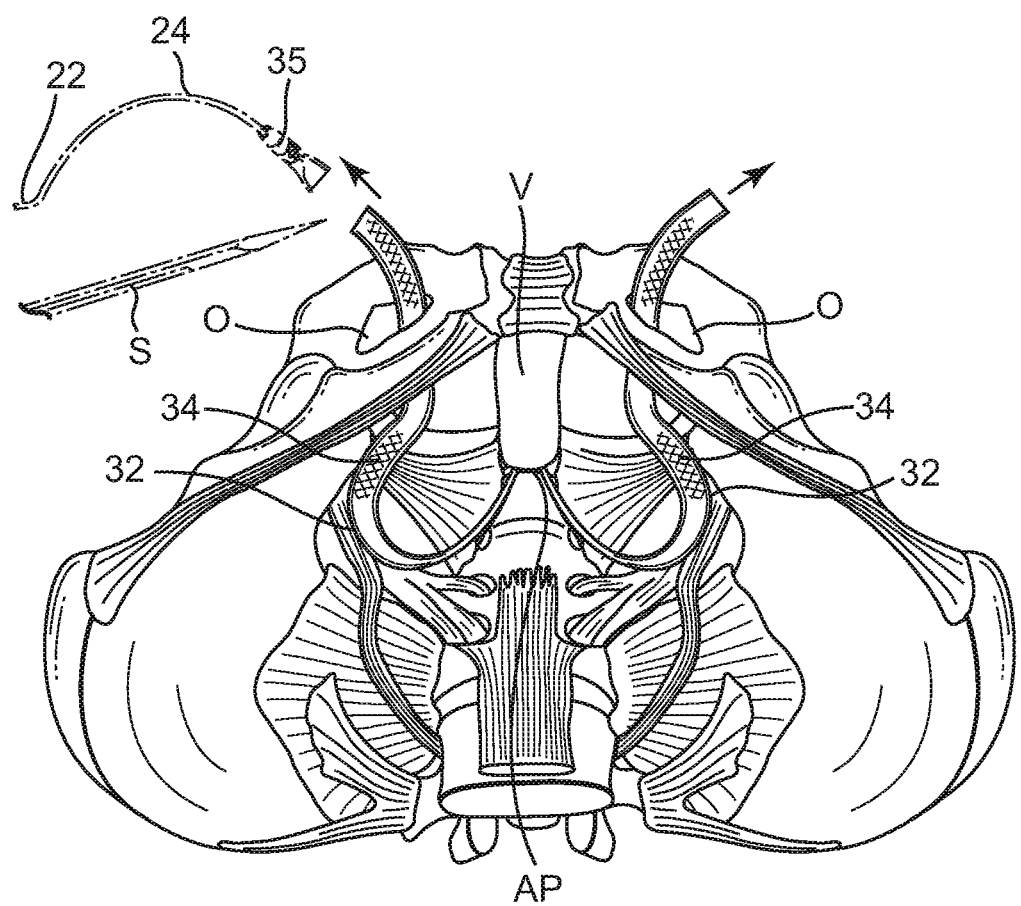

As shown in FIGS. 18, 19 and 20, the same procedure is accomplished on the opposite side of the patient with the opposite end of the implant assembly 30.

Figure 20A:
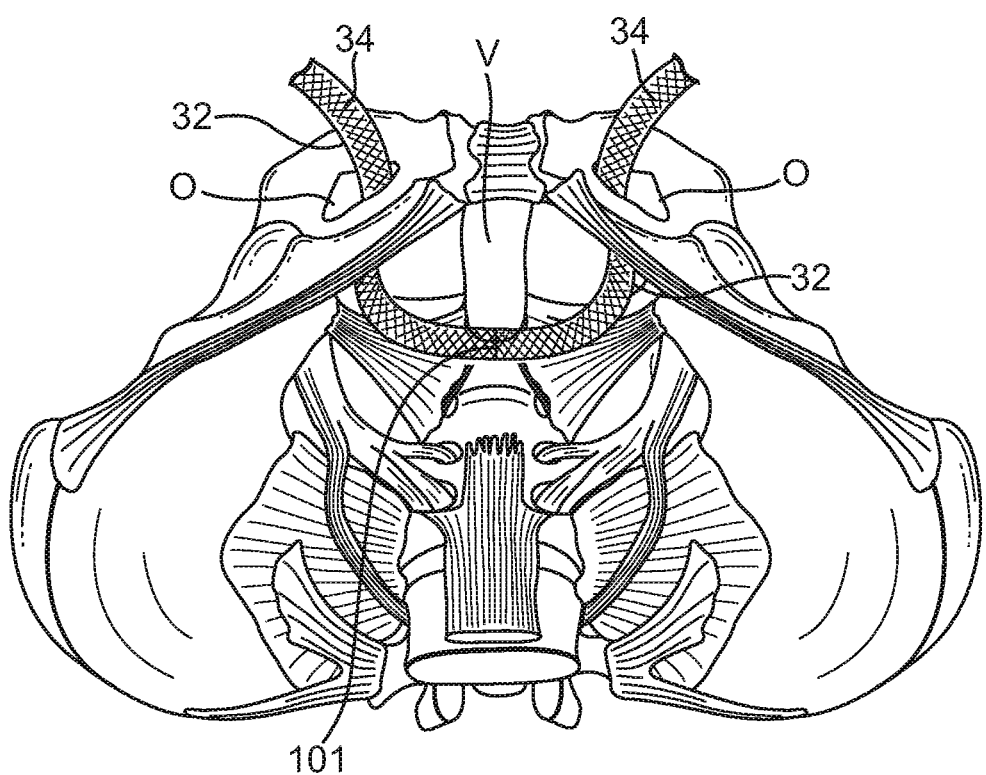
FIG. 20A illustrates the implant attached (e.g. stitched) to the vagina in the region of the apex.

As shown in FIG. 20A, the implant 34 may be fixed to the vaginal wall with two stitches 101 about 1.5 cm from the apex AP. It can also be fixed to the rectum (e.g. in the region or directly to) with two other stitches. The implant 34 is between the vagina and rectum. Its passage through the levator ani is on both sides, the fixation point of the vaginal vault suspension.

Figure 21:
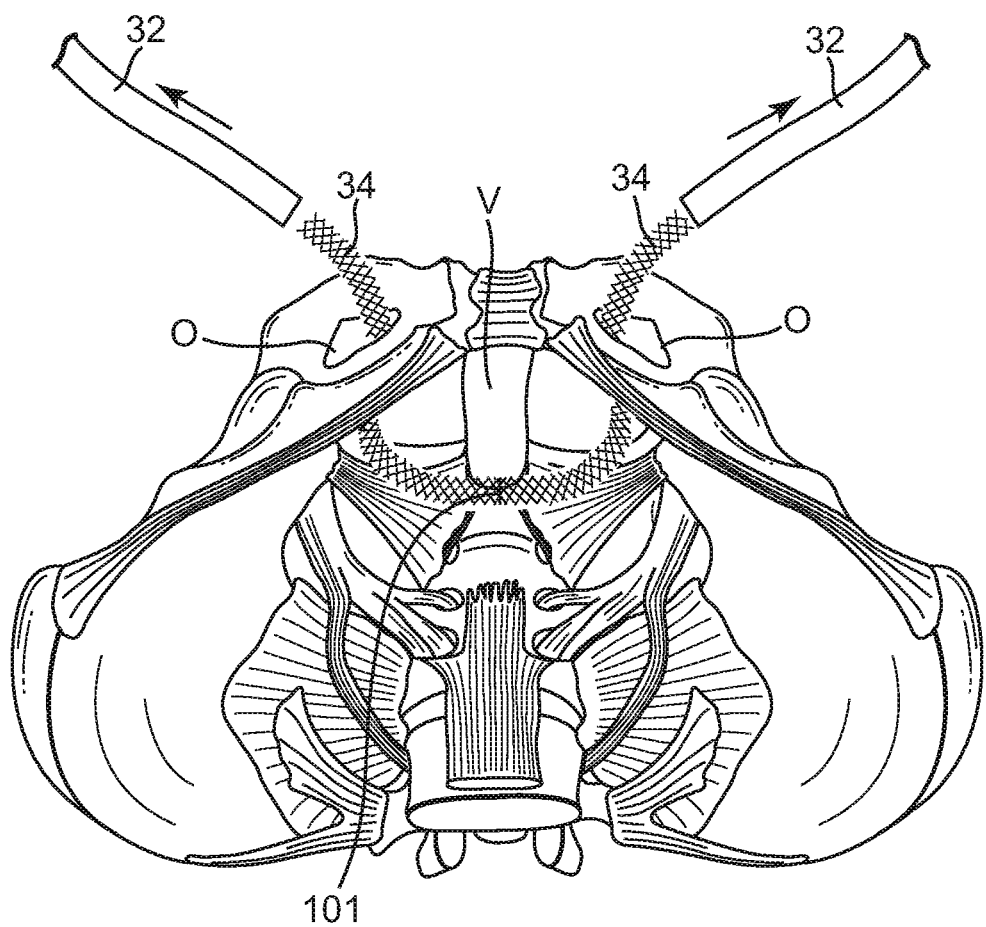
Figure 22:
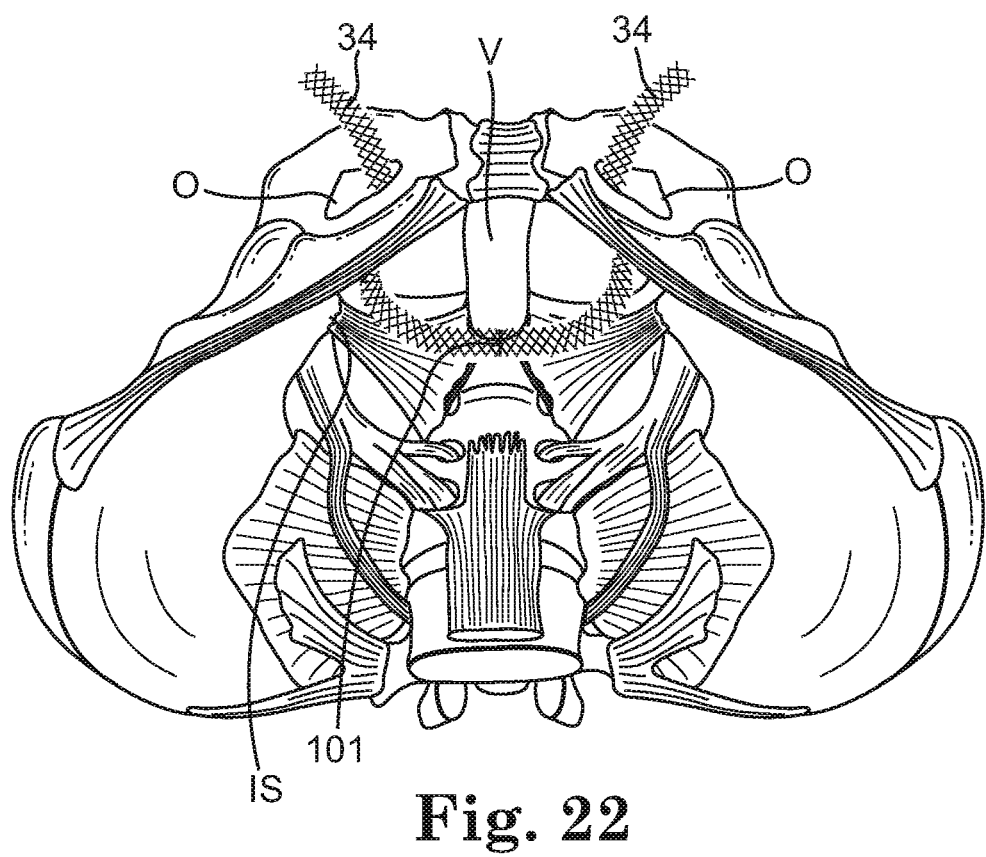

Once the implant 34 is implanted, the insertion sheaths 32 may be removed as shown in FIG. 21. FIG. 22 shows the corrected prolapse with the vagina V supported by implant 34.

The posterior repair can be accomplished with posterior perineo-myorraphy and some times plications of the rectal fascia. The vaginal wall may be closed with a suture from the vaginal apex to the lowest region of the perineum.

Anterior Route Fixation

The stabilization of the vaginal vault can also be accomplished with an anterior route (e.g. if the surgeon prefers this route for surgical reasons). The implant 34 may be implanted by anterior dissection of the anterior vaginal wall. The bladder is dissected off the vagina. The para-vesical space is opened on both sides going to the ischial spines IS.

The needles 10 and 20 may be used similarly in the posterior procedure and the implant can be fit through muscular wall in both sides. The implant 34 may be fixed to the anterior part of the vaginal vault at the apex AP.

All patents, patent applications, journal articles and publications mentioned herein are expressly incorporated by reference in their entirety.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method for correcting vaginal prolapse in a patient, comprising:

providing a first surgical instrument and a second surgical instrument, the first and second surgical instruments including a handle and a needle portion, the needle portion having a straight portion emerging from the handle and a generally helical portion having a distal end region, wherein the straight portion of the first and second instruments has a longitudinal axis and the generally helical portion has an axis that is not parallel to the axis of the straight portion;

providing a mesh implant;

creating a vaginal incision;

passing the distal end region of the first surgical instrument through the obturator foramen on a first side of the patient and then through the vaginal incision;

associating the implant with the first surgical instrument;

passing the distal end region of the second surgical instrument through the obturator foramen on a second side of the patient and then through the vaginal incision;

associating the implant with the second surgical instrument;

moving the distal end region of the first surgical instrument from the vaginal incision through the patient's obturator foramen on the first side of the patient with an end of the implant associated with the distal end region of the first surgical instrument; and moving the distal end region of the second surgical instrument from the vaginal incision through the patient's obturator foramen on the second side of the patient with an end of the implant associated with the distal end region of the second surgical instrument.

2. The method of claim 1, wherein creating a vaginal incision includes creating a vaginal incision in a region of an apex of the vagina.

3. The method of claim 1, wherein providing first and second surgical instruments includes providing at least one of the first and second surgical instruments adapted for right-handed use and the other of the first and second surgical instruments adapted for left-handed use.

4. The method of claim 1, further including attaching the implant to the vagina.

5. The method of claim 1, wherein providing a mesh implant includes providing a mesh implant having a separable sleeve.

6. The method of claim 5, wherein the separable sleeve includes at least one dilating connector.

7. The method of claim 6, wherein the at least one dilating connector includes opposing dilating connectors.

8. The method of claim 1, wherein providing a mesh implant includes providing a mesh implant having a separable sleeve with a pair of dilating connectors.

9. The method of claim 1, wherein passing the distal end region of the first surgical instrument through the obturator foramen includes passing the distal end region of the first surgical instrument through the inferior part of the obturator foramen.

10. The method of claim 9, wherein passing the distal end region of the first surgical instrument through the inferior part of the obturator foramen includes passing the distal end region through the inferior part of the obturator foramen above the ischiopubic ramus.

11. A surgical method for correcting vaginal prolapse in a patient, comprising:

providing a first surgical instrument including a handle and a needle portion, the needle portion having a straight portion emerging from the handle and a generally helical portion having a distal end region, wherein the straight portion has a longitudinal axis and the generally helical portion has an axis that is not parallel to the axis of the straight portion;

providing a second surgical instrument including a handle and a needle portion, the needle portion having a distal end region;

providing a mesh implant having a separable sleeve and one or more end dilators;

creating a vaginal incision;

passing the distal end region of the first surgical instrument through the obturator foramen on a first side of the patient and then through the vaginal incision;

associating the implant with the first surgical instrument;

passing the distal end region of the second surgical instrument through the obturator foramen on a second side of the patient and then through the vaginal incision;

associating the implant with the second surgical instrument;

moving the distal end region of the first surgical instrument from the vaginal incision back through the patient's obturator foramen on the first side of the patient with an end of the implant associated with the distal end region of the first surgical instrument; and moving the distal end region of the second surgical instrument from the vaginal incision through the patient's obturator foramen on the second side of the patient with an end of the implant associated with the distal end region of the second surgical instrument.

12. The method of claim 11, wherein creating a vaginal incision includes creating a vaginal incision in a region of an apex of the vagina.

13. The method of claim 11, wherein providing the first surgical instrument includes providing a surgical instrument adapted for right-handed use.

14. The method of claim 11, wherein providing the first surgical instrument includes providing a surgical instrument adapted for left-handed use.

15. The method of claim 11, further including attaching the implant to the vagina.

16. The method of claim 11, wherein passing the distal end region of the first surgical instrument through the obturator foramen includes passing the distal end region of the first surgical instrument through the inferior part of the obturator foramen.

17. The method of claim 16, wherein passing the distal end region of the first surgical instrument through the inferior part of the obturator foramen includes passing the distal end region through the inferior part of the obturator foramen above the ischiopubic ramus.

* * * * *

UNITED STATES PATENT AND TRADEMARK OFFICE
CERTIFICATE OF CORRECTION

PATENT NO.        : 8,753,260 B2
APPLICATION NO.   : 13/235694
DATED             : June 17, 2014
INVENTOR(S)       : Mellier Page 1 of 2

It is certified that error appears in the above-identified patent and that said Letters Patent is hereby corrected as shown below:

On the Title Page, in item (56), under "OTHER PUBLICATIONS", in Column 2, Line 2, delete "Oct. 25, 2003" and insert -- Oct. 15, 2003 --, therefor.

On Title Page 3, in item (56), under "OTHER PUBLICATIONS", in Column 2, Line 14, delete "par vole" and insert -- par voie --, therefor; Column 2, Line 53, delete "Ivan et all," and insert -- Ivan et al., --, therefor; Column 2, Line 68, delete "Windows" and insert -- Worldwide --, therefor.

On Title Page 4, in item (56), under "OTHER PUBLICATIONS", in Column 1, Line 30, delete "Magentic" and insert -- Magnetic --, therefor; Column 1, Line 56, delete "383-390" and insert -- 388-390 --, therefor.

On Title Page 4, in item (56), under "OTHER PUBLICATIONS", in Column 2, Line 20, delete "Stess" and insert -- Stress --, therefor; Column 2, Line 26, delete "Prcedure)"" and insert -- Procedure)" --, therefor; Column 2, Line 56, delete "Tranobturator" and insert -- Transobturator --, therefor.

On Title Page 5, in item (56), under "OTHER PUBLICATIONS", in Column 1, Line 7, delete "1997." and insert -- (1997). --, therefor; Column 1, Line 28, delete "Spincter:" and insert -- Sphincter: --, therefor; Column 1, Line 34, delete "tuck')"" and insert -- 'tuck')" --, therefor.

On Title Page 5, in item (56), under "OTHER PUBLICATIONS", in Column 2, Line 8, delete "Urinary Symtoms" and insert -- Urinary Symptoms --, therefor; Column 2, Line 25, delete "Pappa," and insert -- Papa, --, therefor.

On Title Page 6, in item (56), under "OTHER PUBLICATIONS", in Column 2, Line 19, delete "perinial," and insert -- perineal, --, therefor; Column 2, Line 27, delete "eg." and insert -- e.g. --, therefor; Column 2, Line 60, delete "clincal" and insert -- clinical --, therefor.

Signed and Sealed this
Twenty-first Day of October, 2014

Michelle K. Lee
*Deputy Director of the United States Patent and Trademark Office*

CERTIFICATE OF CORRECTION (continued)
U.S. Pat. No. 8,753,260 B2

In the Specification

In Column 3, Line 11, delete "0.5 mm" and insert -- 0.5 mm. --, therefor.

In Column 7, Line 20, delete "sleeve 32" and insert -- sheath 32 --, therefor.